(12) United States Patent
Wu et al.

(10) Patent No.: US 9,222,910 B2
(45) Date of Patent: Dec. 29, 2015

(54) UNDERFILL MANAGEMENT SYSTEM FOR A BIOSENSOR

(75) Inventors: Huan-Ping Wu, Granger, IN (US); Eric Maurer, South Bend, IN (US)

(73) Assignee: BAYER HEALTHCARE LLC, Whippany, NJ (US)

(*) Notice: Subject to any disclaimer, the term of this patent is extended or adjusted under 35 U.S.C. 154(b) by 508 days.

(21) Appl. No.: 13/154,650

(22) Filed: Jun. 7, 2011

(65) Prior Publication Data

US 2011/0297557 A1 Dec. 8, 2011

Related U.S. Application Data

(60) Provisional application No. 61/352,234, filed on Jun. 7, 2010.

(51) Int. Cl.
*G01N 27/327* (2006.01)
*G01N 33/66* (2006.01)
*G01N 33/487* (2006.01)

(52) U.S. Cl.
CPC ...... *G01N 27/3274* (2013.01); *G01N 33/48771* (2013.01)

(58) Field of Classification Search
CPC .................. G01N 27/3274; G01N 33/48771
See application file for complete search history.

(56) References Cited

U.S. PATENT DOCUMENTS

| 4,431,004 | A | 2/1984 | Bessman et al. |
| 5,352,351 | A | 10/1994 | White et al. |
| 5,582,697 | A | 12/1996 | Ikeda et al. |
| 5,620,579 | A | 4/1997 | Genshaw et al. |
| 5,653,863 | A | 8/1997 | Genshaw et al. |
| 6,120,676 | A | 9/2000 | Heller et al. |

(Continued)

FOREIGN PATENT DOCUMENTS

| DE | 202005020335 | 5/2006 |
| WO | 03091717 | 4/2003 |

(Continued)

OTHER PUBLICATIONS

International Searching Authority, "International Search Report and Written Opinion for PCT/US2011/039382", Jan. 16, 2012, Publisher: European Patent Office.

(Continued)

*Primary Examiner* — Luan Van
*Assistant Examiner* — Steven Rosenwald
(74) *Attorney, Agent, or Firm* — Nixon Peabody LLP

(57) ABSTRACT

A biosensor system including the underfill management system determines the analyte concentration in a sample from the at least one analytic output signal value. The underfill management system includes an underfill recognition system and an underfill compensation system. The underfill recognition system determines whether the test sensor initially is substantially full-filled or underfilled, indicates when the sample volume is underfilled so that additional sample may be added to the test sensor, and starts or stops the sample analysis in response to the sample volume. The underfill recognition system also may determine the initial degree of underfill. After the underfill recognition system determines the initial fill state of the test sensor, the underfill compensation system compensates the analysis based on the initial fill state of the test sensor to improve the measurement performance of the biosensor system for initially underfilled test sensors.

23 Claims, 17 Drawing Sheets

(56) References Cited

U.S. PATENT DOCUMENTS

| | | | |
|---|---|---|---|
| 6,153,069 | A | 11/2000 | Pottgen et al. |
| 6,233,471 | B1 | 5/2001 | Berner et al. |
| 6,391,645 | B1 | 5/2002 | Huang et al. |
| 6,413,411 | B1 | 7/2002 | Pottgen et al. |
| 6,448,067 | B1 | 9/2002 | Tajnafoi |
| 6,531,040 | B2 | 3/2003 | Musho et al. |
| 6,576,117 | B1 | 6/2003 | Iketaki et al. |
| 6,743,635 | B2 * | 6/2004 | Neel et al. ............. 436/95 |
| 6,797,150 | B2 | 9/2004 | Kermani et al. |
| 7,118,668 | B1 | 10/2006 | Edelbrock et al. |
| 7,122,110 | B2 | 10/2006 | Deng et al. |
| 7,132,041 | B2 | 11/2006 | Deng et al. |
| 7,195,704 | B2 | 3/2007 | Kermani et al. |
| 7,351,323 | B2 | 4/2008 | Iketaki et al. |
| 7,488,601 | B2 | 2/2009 | Burke et al. |
| 7,491,310 | B2 | 2/2009 | Okuda et al. |
| 7,537,684 | B2 | 5/2009 | Sato et al. |
| 7,966,859 | B2 | 6/2011 | Wu et al. |
| 8,002,965 | B2 | 8/2011 | Beer et al. |
| 2002/0084196 | A1 | 7/2002 | Liamos et al. |
| 2002/0146835 | A1 | 10/2002 | Modzelewski et al. |
| 2002/0160517 | A1 | 10/2002 | Modzelewski et al. |
| 2003/0098233 | A1 | 5/2003 | Kermani et al. |
| 2004/0256248 | A1 | 12/2004 | Burke et al. |
| 2005/0023154 | A1 | 2/2005 | Kermani et al. |
| 2008/0093230 | A1 * | 4/2008 | Diamond et al. ............. 205/792 |
| 2008/0173552 | A1 | 7/2008 | Wu et al. |
| 2008/0179197 | A1 | 7/2008 | Wu |
| 2009/0095071 | A1 | 4/2009 | Wu et al. |
| 2009/0099787 | A1 | 4/2009 | Carpenter et al. |
| 2009/0177406 | A1 | 7/2009 | Wu |

FOREIGN PATENT DOCUMENTS

| | | | |
|---|---|---|---|
| WO | 2005073393 | 8/2005 | |
| WO | 2005078437 | 8/2005 | |
| WO | 2006079797 | 8/2006 | |
| WO | 2007013915 | 2/2007 | |
| WO | 2007040913 | 4/2007 | |
| WO | WO 2007131036 A1 * | 11/2007 | ........... G01N 33/487 |
| WO | 2008049075 | 4/2008 | |
| WO | 2009108239 | 9/2009 | |
| WO | 2010077660 | 7/2010 | |
| WO | 2011059670 | 5/2011 | |

OTHER PUBLICATIONS

Panteleon, et al., "The Role of the Independent Variable to Gluscose Sensor Calibration", "Diabetes Technology & Therapeutics", 2003, pp. 401-441, vol. 5, No. 3.

International Searching Authority, "International Search Report and Written Opinion for PCT/US2007/068034", Sep. 24, 2007, Publisher: European Patent Office, Published in: EP.

International Searching Authority, "International Search Report and Written Opnion for PCT/US2010/053765", Mar. 9, 2011, Publisher: European Patent Office, Published in: EP.

* cited by examiner

UNDERFILL MANAGEMENT SYSTEM FOR A BIOSENSOR

REFERENCE TO RELATED APPLICATIONS

This application claims the benefit of U.S. Provisional Application No. 61/352,234 entitled "Underfill Management System for a Biosensor" filed Jun. 7, 2010, which is incorporated by reference in its entirety.

BACKGROUND

Biosensor systems provide an analysis of a biological fluid, such as whole blood, serum, plasma, urine, saliva, interstitial, or intracellular fluid. Typically, the systems include a measurement device that analyzes a sample in a test sensor. The sample usually is in liquid form and in addition to being a biological fluid, may be the derivative of a biological fluid, such as an extract, a dilution, a filtrate, or a reconstituted precipitate. The analysis performed by the biosensor system determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. The analysis may be useful in the diagnosis and treatment of physiological abnormalities. For example, a diabetic individual may use a biosensor system to determine the glucose level in whole blood for adjustments to diet and/or medication.

Biosensor systems may be designed to analyze one or more analytes and may use different volumes of biological fluids. Some systems may analyze a single drop of whole blood including red blood cells, such as from 0.25-15 microliters (µL) in volume. Biosensor systems may be implemented using bench-top, portable, and like measurement devices. Portable measurement devices may be hand-held and allow for the identification and/or quantification of one or more analytes in a sample. Examples of portable measurement devices include the Ascensia® Breeze® and Elite® meters of Bayer HealthCare in Tarrytown, N.Y., while examples of bench-top measurement devices include the Electrochemical Workstation available from CH Instruments in Austin, Tex.

In electrochemical biosensor systems, the analyte concentration is determined from an electrical signal generated by an electrochemical oxidation/reduction or redox reaction of a measurable species when an excitation signal is applied to the sample. The measurable species may be ionized analyte or an ionized species responsive to the analyte, such as a mediator. The excitation signal may be a potential or current and may be constant, variable, or a combination thereof such as when an AC signal is applied with a DC signal offset. The excitation signal may be applied as a single pulse or in multiple pulses, sequences, or cycles.

Electrochemical biosensor systems usually include a measurement device having electrical contacts that connect with the electrical conductors of a test sensor. The electrical conductors may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes.

The test sensor may include reagents that react with the analyte in the sample. The reagents may include an ionizing agent for facilitating the redox reaction of the analyte, as well as mediators or other substances that assist in transferring electrons between the ionized analyte and the electrodes. The ionizing agent may be an analyte specific enzyme, such as glucose oxidase or glucose dehydrogenase, which catalyze the oxidation of glucose. The reagents may include a binder that holds the enzyme and mediator together. A binder is a polymeric material that is at least partially water-soluble and that provides physical support and containment to the reagents while having chemical compatibility with the reagents.

Mediators assist in the transfer of an electron from a first species to a second species. For example, a mediator may assist in the transfer of an electron from the redox reaction between the analyte and the oxidoreductase to or from the surface of the working electrode of the test sensor. A mediator also may assist in the transfer of an electron to or from the surface of the counter electrode to the sample. Mediators may be able to transfer one or more electrons during the conditions of the electrochemical reaction. Mediators may be organotransition metal complexes, such as ferrocyanide/ferricyanide; coordination compound metal complexes, such as ruthenium hexaamine; electroactive organic molecules, such as 3-phenylimino-3H-phenothiazines (PIPT) and 3-phenylimino-3H-phenoxazines (PIPO); and the like.

The test sensor may be placed in the measurement device and a sample introduced into the sample reservoir of the test sensor for analysis. A chemical redox reaction begins between the analyte, the ionizing agent, and any mediator to form an electrochemically measurable species. To analyze the sample, the measurement device applies the excitation signal to electrical contacts connected to the electrical conductors of the test sensor. The conductors convey the electrical signal to the electrodes that convey the excitation into the sample. The excitation signal causes an electrochemical redox reaction of the measurable species, which generates the analytic output signal. The electrical analytic output signal from the test sensor may be a current (as generated by amperometry or voltammetry), a potential (as generated by potentiometry/galvanometry), or an accumulated charge (as generated by coulometry). The measurement device determines the analyte concentration in response to the analytic output signal from the electrochemical redox reaction of the measurable species.

In amperometry, a potential or voltage is applied to the sample. The electrochemical redox reaction of the measurable species generates current in response to the potential. This current is measured at a fixed time at a substantially constant potential to quantify the analyte in the sample. Amperometry measures the rate at which the measurable species is electrochemical oxidized or reduced to determine the analyte concentration in the sample. Thus, amperometry does not measure the total amount of analyte in the sample, but determines the analyte concentration in the sample based on the electrochemical redox reaction rate of the analyte in response to time. Biosensor systems using amperometry are described in U.S. Pat. Nos. 5,620,579; 5,653,863; 6,153,069; and 6,413,411.

In coulometry, a potential is applied to the sample to exhaustively oxidize or reduce the measurable species within the sample. The applied potential generates a current that is integrated over the time of the electrochemical redox reaction to produce an electrical charge representing the analyte concentration. Coulometry generally attempts to capture the total amount of analyte within the sample, necessitating knowledge of sample volume to determine the analyte concentration in the sample. A biosensor system using coulometry for whole blood glucose measurement is described in U.S. Pat. No. 6,120,676.

In voltammetry, a varying potential is applied to the sample. The electrochemical redox reaction of the measurable species generates current in response to the applied potential. The current is measured as a function of applied potential to quantify the analyte in the sample. Voltammetry generally measures the rate at which the measurable species is oxidized or reduced to determine the analyte concentration in the sample. Thus, voltammetry does not measure the total amount of analyte in the sample, but determines the analyte concentration in the sample based on the electrochemical redox reaction rate of the analyte in response to potential.

In gated amperometry and gated voltammetry, pulsed excitations may be used as described in U.S. Pat. Pubs. 2008/0173552, filed Dec. 19, 2007, and 2008/0179197, filed Feb. 26, 2006, respectively.

The measurement performance of a biosensor system is defined in terms of accuracy, which reflects the combined effects of random and systematic error components. Systematic error, or trueness, is the difference between the average value determined from the biosensor system and one or more accepted reference values for the analyte concentration of the sample. Trueness may be expressed in terms of mean bias, with larger mean bias values representing lower trueness and thereby contributing to less accuracy. Precision is the closeness of agreement among multiple analyte readings in relation to a mean. One or more errors in the analysis contribute to the bias and/or imprecision of the analyte concentration determined by the biosensor system. A reduction in the analysis error of a biosensor system therefore leads to an increase in accuracy and thus an improvement in measurement performance.

Bias may be expressed in terms of "absolute bias" or "percent bias". Absolute bias may be expressed in the units of the measurement, such as mg/dL, while percent bias may be expressed as a percentage of the absolute bias value over 100 mg/dL or the reference analyte concentration of the sample. For glucose concentrations less than 100 mg/dL, percent bias is defined as (the absolute bias over 100 mg/dL)*100. For glucose concentrations of 100 mg/dL and higher, percent bias is defined as the absolute bias over the reference analyte concentration*100. Accepted reference values for the analyte glucose in whole blood samples may be obtained with a reference instrument, such as the YSI 2300 STAT PLUS™ available from YSI Inc., Yellow Springs, Ohio. Other reference instruments and ways to determine percent bias may be used for other analytes.

The percent of analyses that fall within a "percent bias limit" of a selected percent bias boundary indicate the percent of the determined analyte concentrations that are close to a reference concentration. Thus, the limit defines how close the determined analyte concentrations are to the reference concentration. For instance, 95 out of 100 performed analysis (95%) falling within a ±10% percent bias limit is a more accurate result than 80 out of 100 performed analysis (80%) falling within a ±10% percent bias limit. Similarly, 95 out of 100 performed analyses falling within a ±5% percent bias limit is a more accurate result than 95 out of 100 performed analyses falling within a ±10% percent bias limit. Thus, an increase in the percentage of analyses falling within a selected percent bias limit or within a narrower percent bias limit represents an increase in the measurement performance of the biosensor system.

The mean may be determined for the percent biases determined from multiple analyses using test sensors to provide a "mean percent bias" for the multiple analyses. As a mean percent bias may be determined, a "percent bias standard deviation" also may be determined to describe how far the percent biases of multiple analyses are away from each other. Percent bias standard deviation may be considered an indicator of the precision of multiple analyses. Thus, a decrease in percent bias standard deviation represents an increase in the measurement performance of the biosensor system.

Increasing the measurement performance of the biosensor system by reducing errors from these or other sources means that more of the analyte concentrations determined by the biosensor system may be used for accurate therapy by the patient when blood glucose is being monitored, for example. Additionally, the need to discard test sensors and repeat the analysis by the patient also may be reduced.

A test case is a collection of multiple analyses (data population) arising under substantially the same testing conditions. For example, determined analyte concentration values have typically exhibited poorer measurement performance for user self-testing than for health care professional ("HCP") testing and poorer measurement performance for HCP-testing than for controlled environment testing. This difference in measurement performance may be reflected in larger percent bias standard deviations for analyte concentrations determined through user self-testing than for analyte concentrations determined through HCP-testing or through controlled environment testing. A controlled environment is an environment where physical characteristics and environmental aspects of the sample may be controlled, preferably a laboratory setting. Thus, in a controlled environment, hematocrit concentrations can be fixed and actual sample temperatures can be known and compensated. In a HCP test case, operating condition errors may be reduced or eliminated. In a user self-testing test case, such as a clinical trial, the determined analyte concentrations likely will include error from all types of error sources.

The analytic output signal is used by the biosensor system to determine the analyte concentration of the sample. Biosensor systems may provide an analytic output signal during the analysis of the sample that includes one or multiple errors. These errors may be reflected in an abnormal output signal, such as when one or more portions or the entire output signal is non-responsive or improperly responsive to the analyte concentration of the sample. These errors may be from one or more error contributors, such as the physical characteristics of the sample, the environmental aspects of the sample, the operating conditions of the system, and the like. Physical characteristics of the sample include the hematocrit (red blood cell) concentration of whole blood, interfering substances, and the like. Interfering substances include ascorbic acid, uric acid, acetaminophen, and the like. Environmental aspects of the sample include temperature and the like. Operating conditions of the system include underfill conditions when the sample size is not large enough, slow-filling of the sample, intermittent electrical contact between the sample and one or more electrodes in the test sensor, degradation of the reagents that interact with the analyte, and the like. There may be other contributors or a combination of contributors that cause errors.

If a test sensor is underfilled with sample, the test sensor may provide an inaccurate analysis of the analyte in the sample. Biosensor systems may include an underfill detection system to prevent or screen out analyses associated with sample sizes that are of insufficient volume. Some underfill detection systems have one or more indicator electrodes that may be separate or part of the working, counter, or other electrodes used to determine the concentration of analyte in the sample. Other underfill detection systems have a third or indicator electrode in addition to the counter and working electrodes. Additional underfill detection systems have a sub-element in electrical communication with the counter electrode. Unlike working and counter electrodes, conductive sub-elements, trigger electrodes, and the like are not used to determine the analyte responsive signals generated by the biosensor system. Thus, they may be bare conductive traces, conductors with non-analyte specific reagents, such as mediators, and the like.

Typically, an electrical signal passes between the indicator electrode(s), between the third electrode and the counter electrode, or between the sub-element and the working electrode when a sample is present in the sample reservoir. The electrical signal indicates whether a sample is present and may indicate whether the sample partially or completely fills the sample reservoir. A biosensor using an underfill detection system with a third electrode is described in U.S. Pat. No. 5,582,697. A biosensor using an underfill detection system with a sub-element of the counter electrode is described in U.S. Pat. No. 6,531,040.

Other underfill methods may use an electrical property of the sample that changes with sample volume to determine underfill. For example, U.S. Pat. No. 6,797,150 discloses the use of capacitance to determine if a test sensor is too severely underfilled to analyze or if the test sensor is underfilled but analyzable if the determined concentration is adjusted. Unlike indicator electrode systems that depend only on the sample being conductive, electrical property based systems rely on an electrical property of the sample that changes with sample volume. In the '150 patent, if the test sensor is severely underfilled, the analysis is stopped. If the test sensor is underfilled, but analyzable with adjustment, the method applies the same analysis method used for a fully filled test sensor, but then adjusts the resulting determined analyte concentration with an offset value. Thus, this underfill analysis method can detect and analyze partially underfilled test sensors, but lacks the ability to correct the errors arising from test sensors needing additional sample to be properly analyzed.

While a conventional biosensor systems using an underfill detection system can analyze test sensors having some degree of underfill or reduce erroneous results due to an insufficient sample size by stopping the analysis or by instructing the user to add more sample; these underfill detection/analysis systems typically do not address analysis error arising from sample being added more than once to the test sensor, variances in sample fill rate, or variances in the sample addition profile. Sample addition profile errors arise when the sample does not evenly flow across the reagents.

There is an ongoing need for improved biosensor systems, especially those that may provide accurate and/or precise analyte concentration determination from underfilled test sensors that are subsequently fully filled for analysis. Such an improved biosensor system could compensate for error arising from refilled test sensors, variances in sample fill rates, and/or sample addition profiles. The systems, devices, and methods of the present invention overcome at least one of the disadvantages associated with conventional biosensor systems.

SUMMARY

A method for determining an analyte concentration in a sample includes determining a fill state of a test sensor, signaling for the addition of additional sample to substantially full-fill the test sensor, applying an analytic test excitation signal to the sample, generating at least one analytic output signal value responsive to the concentration of the analyte in the sample and the analytic test excitation signal, compensating underfill error in the at least one analytic output signal value in response to the fill state of the test sensor, and determining an analyte concentration in the sample from the at least one output signal value and the compensating.

A biosensor system, for determining an analyte concentration in a sample including a test sensor having a sample interface in electrical communication with a reservoir formed by the test sensor and a measurement device having a processor connected to a sensor interface, the sensor interface having electrical communication with the sample interface, and the processor having electrical communication with a storage medium. The processor determines the fill state of a test sensor, signals for the addition of additional sample to substantially full-fill the test sensor, instructs a charger to apply an analytic test excitation signal to the sample, measures at least one analytic output signal value responsive to the concentration of the analyte in the sample and the analytic test excitation signal, compensates underfill error in the at least one analytic output signal value in response to the fill state of the test sensor, and determines an analyte concentration in the sample from the at least one output signal value and the compensating.

A method for determining an analyte concentration in a sample includes applying a regular polling sequence and an extended polling sequence to the sample, the extended polling sequence including at least one different extended input pulse; and generating at least one analytic output signal responsive to the concentration of the analyte in the sample. The method further includes selecting an error parameter responsive to the at least one different extended input pulse, determining at least one slope deviation value from the error parameter, and determining the analyte concentration in the sample from the at least one analytic output signal and a slope compensation equation responsive to the at least one index function, where the slope compensation equation includes at least one reference correlation and at least one slope deviation.

A method for determining an analyte concentration in a sample includes sequentially detecting sample filling of a test sensor, where the sequentially detecting includes determining when two different pairs of electrodes of the test sensor are contacted by the sample, generating at least one analytic output signal responsive to the concentration of the analyte in the sample, selecting an error parameter responsive to when the two different pairs of electrodes of the test sensor are contacted by the sample, determining at least one index function responsive to the error parameter, and determining the analyte concentration in the sample from the at least one analytic output signal and a slope compensation equation responsive to the at least one index function, where the slope compensation equation includes at least one reference correlation and at least one slope deviation

BRIEF DESCRIPTION OF THE DRAWINGS

The invention may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

Figure 1A:
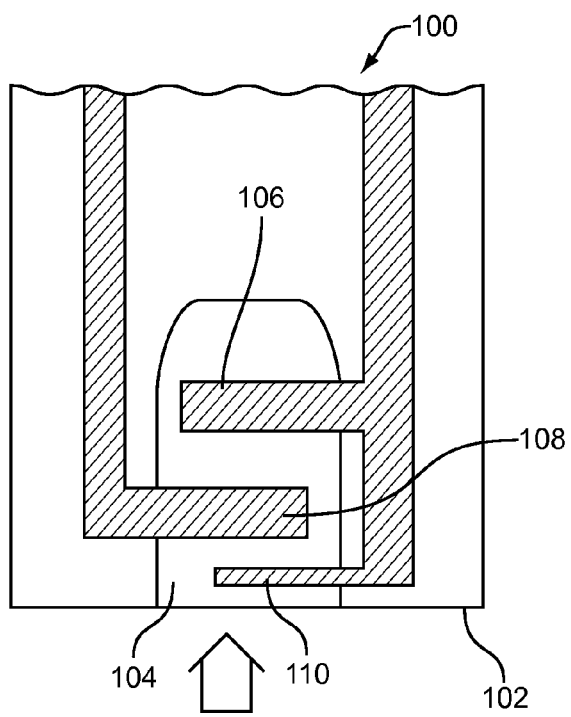
FIG. 1A depicts a schematic representation of a test sensor.

An underfill management system includes an underfill recognition system, which assesses whether to analyze a sample in response to the initial test sensor fill state or to wait for additional sample to be added to the test sensor, and an underfill compensation system, which compensates the analyte analysis for one or more errors arising from the initial and subsequent fills of the test sensor. The underfill recognition system may detect whether a sample is present, determines whether the test sensor initially is substantially full-filled or underfilled, indicates when the sample volume is underfilled so that additional sample may be added to the test sensor, and starts or stops the sample analysis in response to the sample volume. The underfill recognition system also may determine the initial degree of underfill. After the underfill recognition system determines the initial fill state of the test sensor, the underfill compensation system compensates the analysis based on the initial fill state of the test sensor to improve the measurement performance of the biosensor system for initially underfilled test sensors. The underfill recognition system also may determine one or more subsequent fill states, and the underfill compensation system may compensate the analysis based on the one or more subsequent fill states.

The underfill recognition system can be either binary in operation or be able to detect degrees of underfill. If binary, the underfill recognition system determines that sample is present and that sufficient sample is present to proceed with the analysis from the initial fill or that the sample is present but that sufficient sample is not present to proceed with the analysis from the initial fill. If there is insufficient sample to proceed from the initial fill, such a binary system then signals the user to add additional sample, preferably within a predetermined time period, and then directs the system to proceed with the analysis after the sensor is substantially fully filled. The underfill management system then implements one of two underfill compensation systems in response to whether (1) the initial fill resulted in substantial full-fill (SFF) of the test sensor or if (2) a subsequent fill was provided to attain SFF of the test sensor. One or more subsequent fills may be used to SFF the test sensor.

In addition to binary underfill recognition, an underfill recognition system able to detect degrees of underfill can provide the underfill management system with the ability to implement one of at least three underfill compensation systems based on whether the initial fill provided (1) substantial full-fill (SFF), (2) low volume underfill (LUF), or (3) high volume underfill (HUF). Thus, different compensation systems may be implemented in response to different initial fill states. Furthermore, the underfill detection system may be able to determine and implement different compensation systems in response to whether a first subsequent fill resulted in SFF or if a second or third subsequent fill resulted in SFF. For example, a compensation system may be implemented to compensate for the circumstance when the initial fill provides a LUF state, a first subsequent fill provides for a HUF state, and a second subsequent fill provides a SFF state.

After the underfill recognition system determines that the test sensor is SFF, the biosensor system applies analytic test excitations to the sample. The underfill compensation system applies one or more compensation equations in response to the initial and/or subsequent fill state of the test sensor. The compensation equations preferably include index functions extracted from intermediate signals of the analytic output signals and from secondary output signals to adjust a correlation for determining analyte concentrations in the sample from the analytic output signal. The index functions are preferably complex index functions and may be paired with one or more residual functions to provide an underfill compensated analyte concentration.

In a biosensor system with an underfill management system, the underfill recognition system is preferably selected to reduce or substantially eliminate any irreversible alteration of the analyte concentration(s) in the sample before applying the analytic test excitations that electrochemically oxidize or reduce the measurable species to determine the analyte concentration of the sample. "Irreversible alteration" is a change in mass, volume, chemical or electrical properties, a combination thereof, or the like from an original condition to another condition that cannot be undone or essentially returned to the original condition. In analyses that correlate the rate of the electrochemical redox reaction to the analyte concentration, the original reaction rate cannot be obtained once part of the analyte is irreversibly altered by an excitation having a relatively large amplitude and/or long pulse width. In these analyses, the pulse width is more likely to alter the analyte concentration.

Underfill recognition systems that determine the fill state of the test sensor without irreversibly altering the analyte concentration before application of the excitation signal generally fall into two types: (1) sequential detection of sample filling, and (2) polling input signals. However, other underfill recognition systems could be used that preferably do not irreversibly alter the analyte concentration of the sample before the excitation signal is applied and that can provide notification to add additional sample to the test sensor.

Underfill detection systems using sequential detection of sample filling do not irreversibly oxidize, reduce, or otherwise alter the analyte(s) in the sample as relatively short pulse widths are used to detect electrical connection between the consecutively placed electrodes as the sample enters the test sensor. Underfill detection systems using a polling input signal use shorter pulse widths that do not irreversibly oxidize, reduce, or otherwise alter the analyte(s) in the sample. The pulses of the polling input signal contrast with the larger amplitudes or longer pulse widths of the test excitations of the analytic signal that irreversibly oxidize, reduce, or otherwise alter the analyte(s) in the sample.

The underfill recognition system is generally selected on the basis of the electrode design of the test sensor and the desired level of compensation for the underfill management system. The more sophisticated the underfill management system, the better the measurement performance for the system with varying degrees of initial underfill. The test sensor may have various configurations including those with multiple electrodes and conductors. The test sensor may have 2, 3, 4, or more electrodes. Test sensors using a polling input signal for underfill detection generally require two electrodes, while test sensors using the sequential detection of sample filling generally require at least three consecutive electrodes.

A binary underfill recognition system to detect underfill may be implemented on a test sensor 100 as represented in FIG. 1A. The test sensor 100 forms a reservoir 104 including a counter electrode 106 and a working electrode 108 positioned in the reservoir 104. "Positioned in" includes partially or wholly in the reservoir, adjacent or near the reservoir, or like locations where the electrodes would electrically connect with a sample disposed in the reservoir. The counter electrode 106 includes a sub-element 110, which is positioned in the reservoir 104 upstream of the working electrode 108. A mediator may be disposed on the counter electrode 106, on the working electrode 108, in the reservoir 104, a combination thereof, or the like. Other components have been omitted from the test sensor 102 for clarity. The counter electrode 106 and the sub-element 110 may have different redox potentials, such as when a mediator is disposed on the counter electrode 106, but not on the sub-element 110 or when a different mediator system is disposed on the sub-element 110.

The test sensor 100 is SFF is when the test sensor includes enough sample to accurately analyze the concentration of one or more analytes in the sample with the initial SFF compensation system. The volume of sample required to SFF the test sensor for accurate initial SFF compensation may be determined experimentally, theoretically, a combination thereof, or the like. The test sensor 100 may be considered SFF when the working electrode is covered with sample. Substantial full-fill of the test sensor is obtained when at least 85%, preferably at least 90%, and more preferably at least 95% of the sample reservoir volume of the test sensor is filled. For example, a test sensor having a reservoir volume of 0.5 uL, may be considered SFF when at least 0.42 uL of sample is present in the reservoir, preferably when at least 0.45 uL of sample is present in the reservoir, and more preferably when at least 0.48 uL of sample is present in the reservoir. Thus, the underfill recognition system could be configured to determine SFF at one or more of these reservoir fill volumes, depending on the design and placement of the working electrode in the reservoir 104.

When applied to the test sensor 100, a polling input signal generates one or more polling output signals from the sample, which may be used to detect when a sample is present, when the test sensor is underfilled, and when the test sensor is SFF. When the test sensor is SFF, the analytic test excitation signal is applied to the sample and generates one or more output signals, which may be used to determine one or more analyte concentrations in the sample. When underfilled, the underfill detection system requests a user to add more biological fluid to the test sensor. The biosensor may use multiple sample thresholds to detect additional sample in the sensor, such as an initial sample threshold to detect the presence of a sample in the test sensor and a second or refill sample threshold to detect when more sample has been added to the test sensor.

Polling signals have a regular polling sequence of one or more regular input pulses followed by an extended polling sequence of one or more extended input pulses. Regular input pulses are essentially the same, but different regular input pulses may be used. The polling signal essentially is a sequence of polling pulses separated by polling relaxations. During a polling pulse, the electrical signal is on. On includes time periods when an electrical signal is present. During a polling relaxation, the electrical signal is significantly reduced in amplitude in relation to when the electrical signal is on. Reduced includes when the electrical signal is reduced by at least an order of magnitude in relation to when the electrical signal is on. Reduced also includes when the electrical signal is reduced to off. Off includes time periods when an electrical signal is not present. Off does not include time periods when an electrical signal is present but has essentially no amplitude. The electrical signal may switch between on and off by closing and opening an electrical circuit, respectively. The electrical circuit may be opened and closed mechanically, electrically, or the like. Other on/off mechanisms may be used.

The extended polling sequence is part of the polling signal. The extended polling sequence has one or more extended input pulses. One or more or not any of the extended input pulses may be essentially the same as the regular input pulses. At least one extended input pulse in the extended polling sequence is different than the regular input pulses of the regular polling sequence. The different extended input pulse maybe the last or another extended input pulse in the extended polling sequence. Different extended input pulses may step-down, step-up, or a combination thereof, in relation to regular input pulses. Step-down includes extended input pulses where the extended amplitudes decrease with each subsequent input pulse. Step-up includes extended input pulses where the extended amplitudes increase with each subsequent input pulse. The extended polling sequence may generate one or more volume output signals responsive to the sample volume. A volume output signal may be used to determine whether the sample is initially SFF or underfilled.

When a polling signal is applied to a sample in the biosensor, each pulse of the polling signal typically generates a corresponding output pulse from the sample. One or more output pulses form a polling output signal. Each regular input pulse of the regular polling sequence generates a regular output pulse in a sample output signal. The biosensor detects the presence of the sample when at least one of the regular output pulses reaches a sample threshold, and then applies the extended polling sequence. Each extended input pulse of the extended polling sequence generates an extended output pulse in a volume output signal. Different extended input pulses generate different extended output pulses that may be responsive to the fill state of the test sensor.

The regular and extended polling sequences may have pulse widths of less than about 500 milliseconds (ms) and pulse intervals of less than about 2 seconds (sec). The polling sequences may have input pulse widths of less than about 100 ms and pulse intervals of less than about 500 ms. The polling sequence may have input pulse widths in the range of about 0.5 millisecond through about 75 ms and input pulse intervals in the range of about 5 ms through about 300 ms. The polling sequences may have input pulse widths in the range of about 1 millisecond through about 50 ms and input pulse intervals in the range of about 10 ms through about 250 ms. The polling sequence may have input pulse widths of about 5 ms and input pulse intervals of about 125 ms. Thus, the regular and extended polling sequences may each have pulse widths and pulse intervals selected from these or other values, as long as the extended polling sequence includes extended input pulses that are different from the regular inputs pulse widths and pulse intervals.

One or more volume thresholds may be used to detect when a test sensor is initially SFF or underfilled. The test sensor is SFF when a different extended output pulse reaches a selected volume threshold. The test sensor is underfilled and requires more sample for analysis when a different extended output pulse does not reach a volume threshold. When a test sensor is underfilled, the sample covers less of the electrodes in the test sensor than when the test sensor is SFF. Underfill and SFF states may be selected in response to experimental data, theoretical analysis, a desired precision and/or accuracy of the volume or the analysis, the mediator(s) used, the electrode configuration, a combination thereof or the like.

To determine binary underfill through sequential detection using the test sensor 100, a potential having a relatively short pulse width, such as 50 milliseconds or less, may be applied across the working electrode 108 and the counter electrode 106 with the electrically connected sub-element 110. By monitoring the current output as the sample is introduced to the sample reservoir 104, it is possible to determine when the sample contacts the working/sub-element and then the working/counter. If only the working/sub-element is contacted by sample, the biosensor system requests the addition of additional sample to SFF the test sensor 100. While less preferred due to some irreversible alteration of the analyte concentration, binary underfill also may be determined during the initial stage of the application of the analytic input signal. A more detailed description of the use of the analytic input signal to determine underfill may be found in U.S. Pat. Pub. No. 2009/0095071, entitled "Underfill Detection System for a Biosensor".

With a polling signal or sequential detection underfill recognition system, the test sensor 100 can be operated in a binary manner, where the analysis proceeds from an initial SFF or where the biosensor system signals for additional sample to SFF the test sensor after the initial fill, but before the analysis proceeds. When the test sensor is SFF, the biosensor system may apply the test excitation signal immediately after the extended polling period or at other selected time. The underfill management system implements a compensation system for an initially SFF test sensor or for an initially underfilled and subsequently SFF test sensor. As the underfill management system selects the appropriate underfill compensation based on the initial fill state of the test sensor, the underfill compensation system can also compensate for the situation when the analytic input signal is used to detect underfill, however to a lesser extent than when the initial fill state of the test sensor is determined prior to the application of the analytic input signal.

An underfill recognition system that determines one or more degrees of underfill using polling also may be implemented on the test sensor 100 of FIG. 1A. In an underfill recognition system that determines one or more degrees of underfill, multiple different extended input pulses are used to determine the degree of underfill.

In relation to a binary underfill recognition system using polling, additional volume thresholds may be used to detect when a test sensor is initially SFF, or has a range of initially underfilled volumes. The test sensor is SFF when a different extended output pulse reaches a selected volume threshold. The test sensor is underfilled, requires more sample for analysis, and the degree of underfill may be determined when more than one different extended output pulse reaches a volume threshold or reaches one volume threshold but not another volume threshold.

Thus, depending on whether a binary or degree underfill recognition system is used, volume thresholds may be selected to distinguish between multiple fill states, including initial SFF, initial underfill, different initial volumes or volume ranges of underfill, minimum and/or maximum volumes, a combination thereof, or the like. For example, if the degree underfill recognition system detects an initial underfill, volume thresholds may be selected to differentiate a low volume underfill (LUF) from a high volume underfill (HUF) initial fill state.

Volume thresholds may be predetermined threshold values stored in a memory device, obtained from a lookup table, or the like. The predetermined threshold values may have been developed theoretically or from a statistical analysis of laboratory work. Volume thresholds may be measured or calculated threshold values in response to one or more of the polling output signals. Volume thresholds may be selected to identify when a change in one or more output signals is responsive to a volume condition.

The underfill management system may use multiple volume thresholds to determine the volume of the sample or the degree of underfill of a biosensor. When a volume output signal exceeds one volume threshold and not another volume threshold, this volume output signal would indicate the sample volume is between the volumes associated with those volume thresholds. For example, if the volume threshold for an initial LUF is exceeded, but the volume threshold for an initial SFF is not exceeded, this volume output signal would indicate an initial HUF. More volume thresholds may be used to provide more accurate volume determinations.

Cycles in an extended polling sequence may be used to create a buffer or delay for a slow filling sample. While the initial extended output pulse(s) in the volume output signal may indicate underfill, the later or last extended output pulse may indicate SFF when the sample has substantially finished filling. Cycles in an extended polling sequence may be used for other criteria, such as with or without multiple thresholds to determine the volume or a volume range of a sample.

Regular and extended polling sequences will be generated when the last low extended polling output does not meet the volume threshold value. This cycling may continue indefinitely until the sample volume meets the volume threshold or for a selected number of polling sequences. During this time, additional sample may be added to the test sensor to trigger meeting the volume threshold and achieving SFF of the test sensor.

Figure 1B:
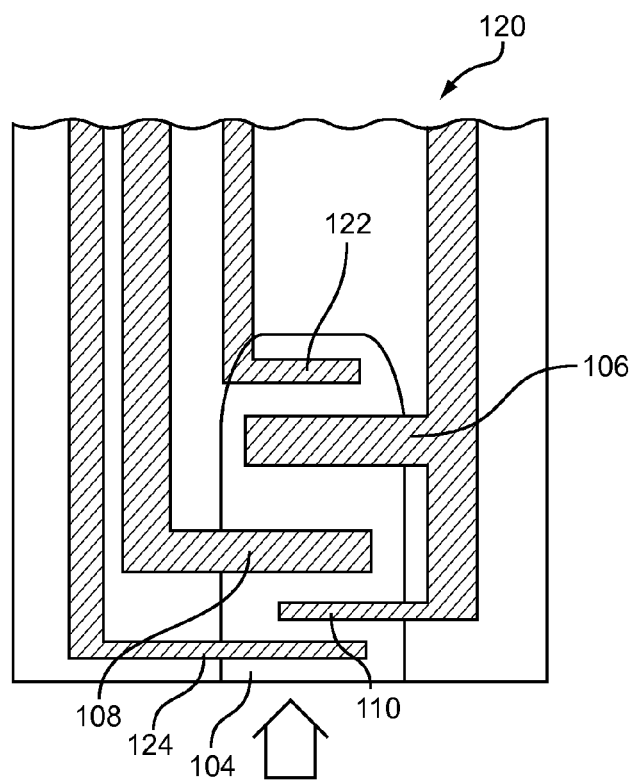
FIG. 1B depicts a schematic representation of a test sensor having indicator electrodes.

An underfill recognition system that determines degrees of underfill using the sequential detection of sample filling across consecutive electrodes may be implemented on a test sensor 120 of FIG. 1B. In addition to the electrodes of the test sensor 100, the test sensor 120 adds additional, electrically independent electrodes 122 and 124. The upstream electrode 124 may be an electrode used to provide a secondary output signal responsive to the hematocrit content of the sample. The downstream electrode 122 may be used to detect that the sample has reached the end of the sample reservoir 104, and thus SFF of the test sensor 120 has occurred.

To determine degrees of underfill for the test sensor 120, relatively short duration potential pulses may be sequentially applied to different electrode pairs to determine which electrode pairs are contacted by sample. For example, electrodes 124 and 110 may be considered a first electrode pair, electrodes 110 and 108 may be considered a second electrode pair, and electrodes 108 and 122 may be considered a third electrode pair. Contact between the hematocrit electrode 124 and the sub-element 110 may be used to indicate sample presence. If the initial fill results in contact between the hematocrit electrode 124 and the sub-element 110, but not between the sub-element 110 and the working electrode 108, an initial LUF has occurred. If the initial fill results in contact between the working electrode 108 and the counter electrode 106, but not between the counter electrode 106 and the additional electrode 122, an initial HUF has occurred. If the initial fill results in contact between the working electrode 108 and the additional electrode 122, an initial SFF has occurred and the analysis can proceed to analyze the analyte with test excitations.

In addition to contact alone, the time that it takes for the sample to cross each consecutive electrode pair also may be used to determine the initial fill state of the test sensor 120. For example, the underfill management system can determine the time that it takes for the sample to contact the sub-element 110 and the working electrode 108 after first contacting the hematocrit electrode 124 and the sub-element 110. If this time falls above a threshold, the test sensor 120 may be considered initially LUF. Similarly, the underfill management system can determine the time that it takes for the sample to contact the working electrode 108 and the additional electrode 122 after first contacting the working electrode 108 and the sub-element 110. If this time falls above a threshold, the test sensor 120 may be considered initially HUF.

The volume threshold or sequential detection factor corresponding to LUF may be selected so that approximately 40% to 50% of the test sensor reservoir is filled, for example. Similarly, the values corresponding to HUF may be selected so that approximately 58% to 70% of the test sensor reservoir filled. Other fill percentages of the test sensor reservoir may be chosen to represent LUF, HUF, or other fill states. Preferably, the threshold or sequential detection factors corresponding to a LUF state indicate an initial underfill where the reagents of the working electrode are not substantially contacted by the sample. Similarly, the threshold or sequential detection factors corresponding to a HUF state preferably indicate an initial underfill where the reagents of at least the working electrode are substantially contacted by the sample.

If sample presence, LUF, or HUF is determined by the underfill recognition system, the system requests additional sample until a SFF occurs. The analytic test excitations are then applied to determine the analyte concentration of the sample. Values from the analytic output signals may be related to analyte concentration through a correlation equation. To determine the underfill compensated analyte concentration, the underfill management system implements the underfill compensation system responsive to the initial fill state, or to the initial fill state in combination with any subsequent fill state.

Figure 2A:
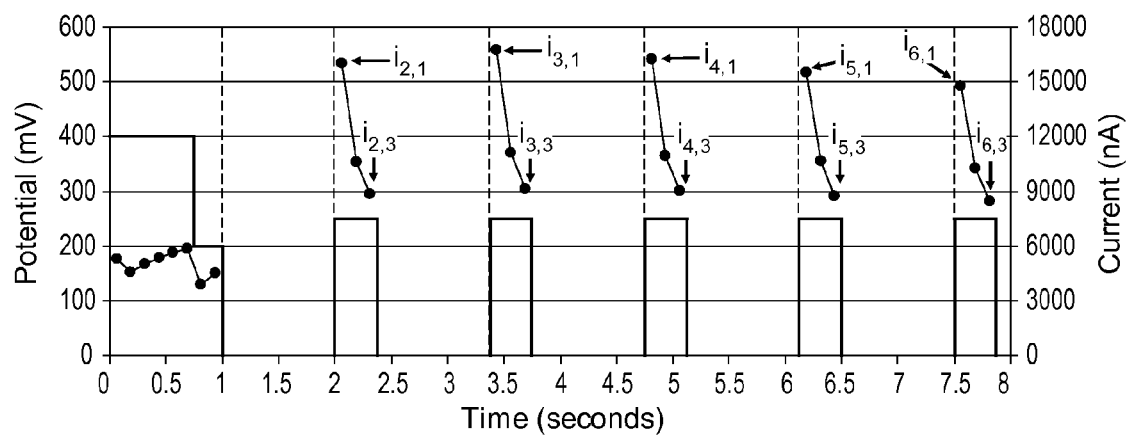
FIG. 2A represents a gated amperometric pulse sequence where the test excitation signal applied to the working and counter electrodes includes multiple pulses.

FIG. 2A represents a gated amperometric pulse sequence where the test excitation signal applied to the working and counter electrodes includes multiple pulses. The analytic output signal current values resulting from the pulses are depicted above each pulse. The intermediate signal current values are depicted as solid circles. Each of the i values is a current value of the analytic output signal responsive to the excitation signal. The first number in the subscript of the i values denotes the pulse number, while the second number in the subscript denotes the order of the output signal as the current values were measured. For example, $i_{2,3}$ denotes the third current value measured for the second pulse.

Index functions, as described below with regards to compensation systems, include one or more indices. Indices represent error parameters and may include ratios of the intermediate signal current values as depicted in FIG. 2A. For example, the intermediate current values may be compared within an individual pulse-signal decay cycle, to provide intra-pulse ratios such as ratios $R3=i_{3,3}/i_{3,1}$, $R4=i_{4,3}/i_{4,1}$, and the like. In these intra-pulse examples, the ratios are formed by dividing the last current value recorded from a pulse by the first current value recorded from the same pulse. In another example, the intermediate current values may be compared between separate pulse-signal decay cycles, such as ratios $R3/2=i_{3,3}/i_{2,3}$, $R4/3=i_{4,3}/i_{3,3}$, and the like. These are inter-pulse ratios where a current value from a later in time pulse is divided by a current value from an earlier in time pulse.

Index functions also may include combinations of ratios extracted from the analytic output signal depicted in FIG. 2A. In one example, an index function may be a linear function which includes a ratio of ratios, such as Ratio3/2=R3/R2, Ratio4/3=R4/R3, and the like. In another example, an index function may include an algebraic or other combination of indices. For example, a combination index, Index-1, may be represented as Index-1=R4/3−Ratio3/2. In another example, a combination index Index-2 may be represented as Index-2= $(R4/3)^p-(Ratio3/2)^q$, where p and q independently are positive numbers.

Figure 2B:
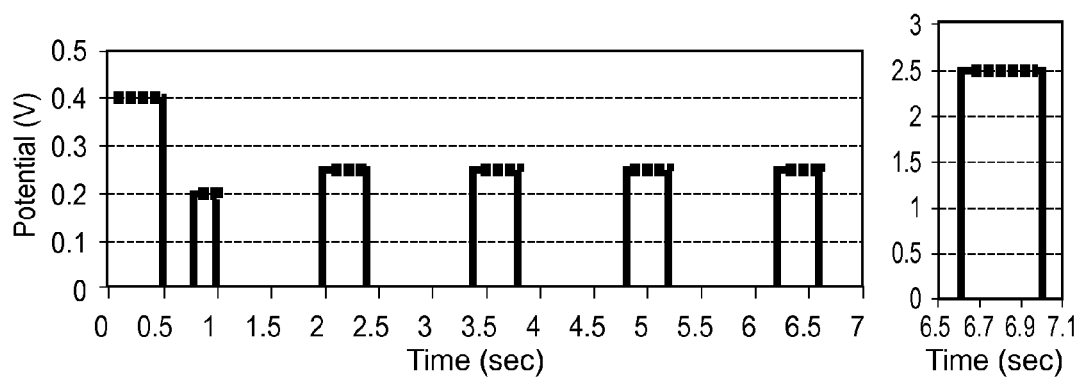
FIG. 2B represents a gated amperometric pulse sequence where the test excitation signal applied to the working and counter electrodes includes multiple pulses, and where a second excitation signal is applied to an additional electrode to generate a secondary output signal.

FIG. 2B represents a gated amperometric pulse sequence where the excitation signal applied to the working and counter electrodes includes multiple pulses, and where a second excitation signal is applied to an additional electrode to generate a secondary output signal responsive to the hematocrit content of the sample. The excitation signal applied to the additional electrode was applied after the completion of the analytic excitation signal, but could be applied at other times. The current values from the additional electrode may be used in an index function relating the current values measured from the additional electrode to the %-Hct of the sample, for example.

While a gated amperometric analytic test excitation signal was used in the following examples of polling and sequential underfill recognition, other test excitation signals could be used that provide for the desired compensation systems.

Figure 3A:
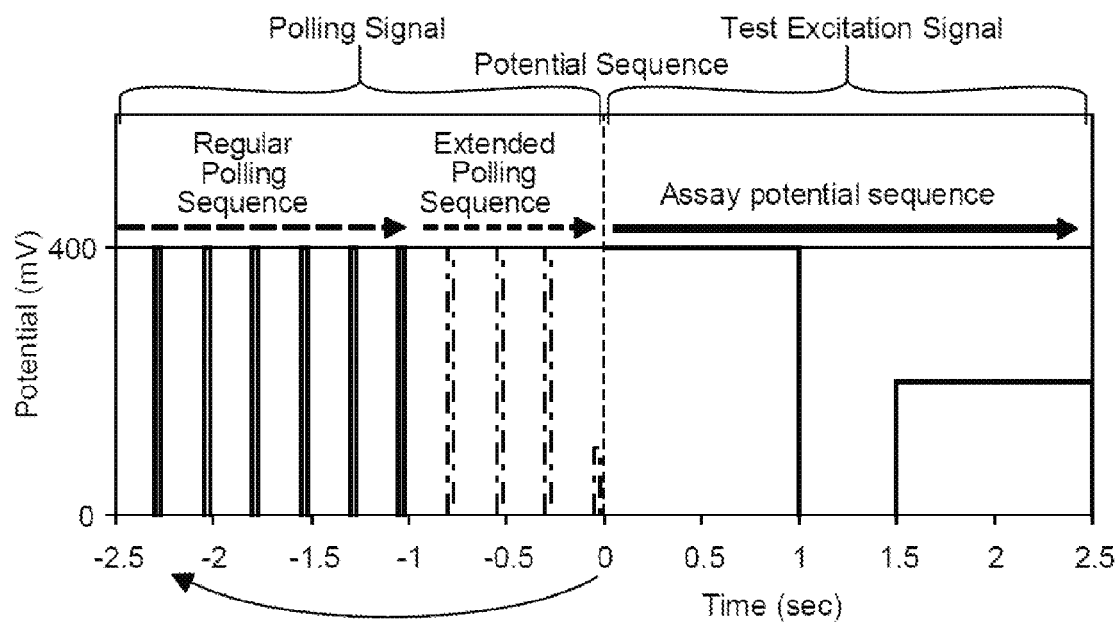
FIG. 3A illustrates the regular and extended polling sequences of a polling input signal and a test excitation signal of a biosensor system having a binary underfill management system.

In FIG. 3A, a polling signal for a binary underfill recognition system is represented having a regular polling sequence of six regular input pulses and an extended polling sequence of four extended input pulses. The extended polling sequence has three similar extended input pulses followed by one different extended input pulse. The three similar extended input pulses have extended amplitudes of about 400 mV, while the different extended input pulse is the last extended input pulse and has an amplitude of about 100 mV. The pulse widths of the regular and extended poling sequences are short, such as at most 50 ms or at most 20 ms. The regular and extended pulse widths are in the range of about 1 ms to about 15 ms or about 5 ms to about 10 ms. The reverse arrow illustrates that the regular polling sequence and/or the extended polling sequence may restart, if desired, such as when no sample is present, the test sensor is initially underfilled, or if other criteria are met or not met. This polling signal may be used with a binary underfill detection system to determine if sample is present in the test sensor, if test sensor is initially SFF, or if the test sensor is initially underfilled.

The analytic potential sequence represented in FIG. 3A has two assay pulses with an excitation pulse width of about 1 second and a relaxation width of about 0.5 second. The first excitation pulse starts essentially at the end of the last extended input pulse in the extended polling sequence. The substantially longer pulse width of the test excitations in relation to the pulse widths of the polling pulses causes irreversible alteration of the analyte concentration of the sample.

Figure 3B:
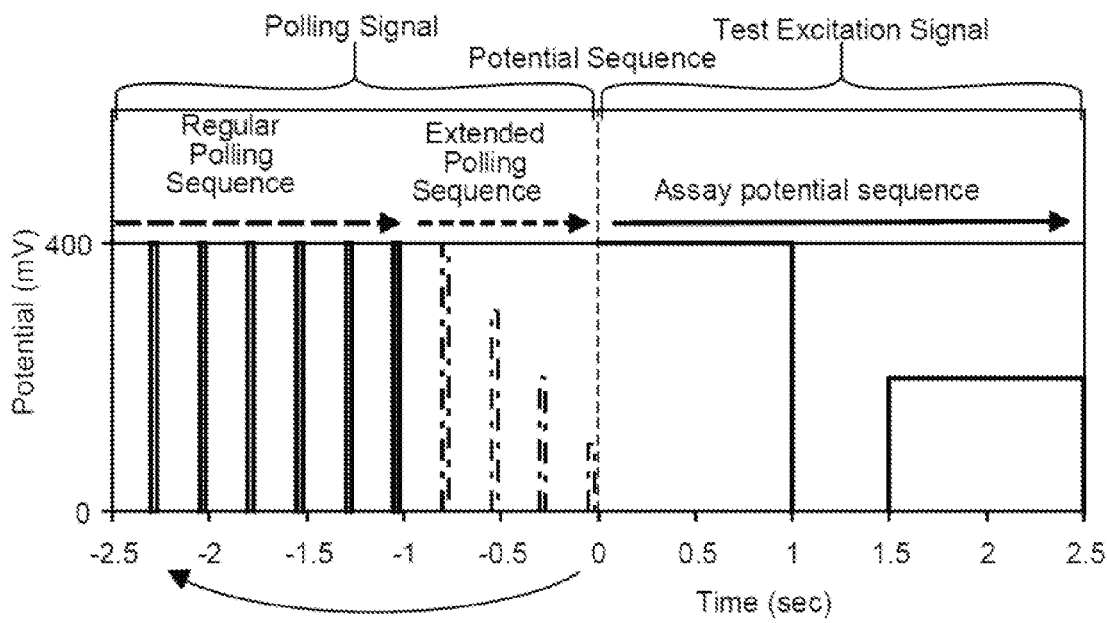
FIG. 3B illustrates the regular and extended polling sequences of a polling input signal and a test excitation signal of a biosensor system having an underfill management system that can distinguish degrees of underfill.

In FIG. 3B, the polling signal for an underfill recognition system capable of distinguishing degrees of underfill has a regular polling sequence of six regular input pulses and an extended polling sequence of four extended input pulses. The extended polling sequence has one similar extended input pulse followed by three different extended input pulses. The similar extended input pulse has an extended amplitude of about 400 mV, which is essentially the same as the regular amplitudes of the regular input pulses. The different extended input pulses step-down or have decreasing extended amplitudes of about 300 mV, about 200 mV, and about 100 mV, which are different than the regular amplitudes of the regular input pulses. This polling signal may be used with an underfill recognition system capable of distinguishing degrees of underfill to determine if sample is present in the test sensor, if test sensor is initially SFF, if the test sensor is initially LUF, or if the test sensor is initially HUF. The polling signal may be used to distinguish additional degrees of underfill.

Polling output signals include sample and volume output signals. Sample output signals are generated in response to regular polling sequences. Volume output signals are generated in response to extended polling sequences. The sample output signals may have a current in the range of about 5 nA to about 800 nA, about 50 nA to about 500 nA, about 100 nA to about 400 nA, or about 200 nA to about 300 nA. The volume output signals may have a current in the range of about 5 nA to about 800 nA, about 50 nA to about 500 nA, about 100 nA to about 400 nA, or about 200 nA to about 300 nA. Other output current values may be obtained in response to the polling input signals based on the nature of the sample and the temperature of the analysis. Preferably, different threshold values may be selected for different temperature ranges.

Figure 3C:
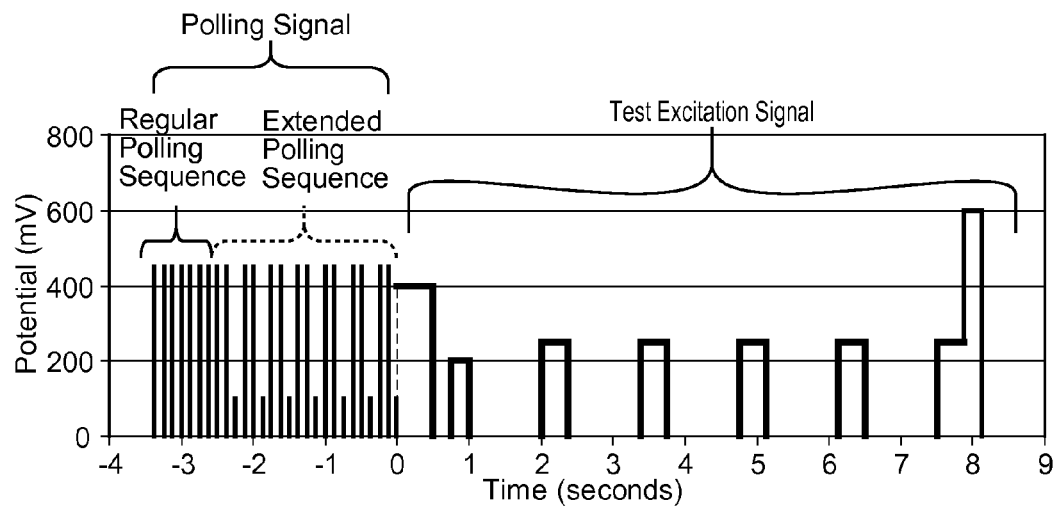
FIG. 3C and FIG. 3D illustrate the regular and extended polling sequences of other polling input signals and other test excitation signals of biosensor systems with a binary underfill management system.
Figure 3D:
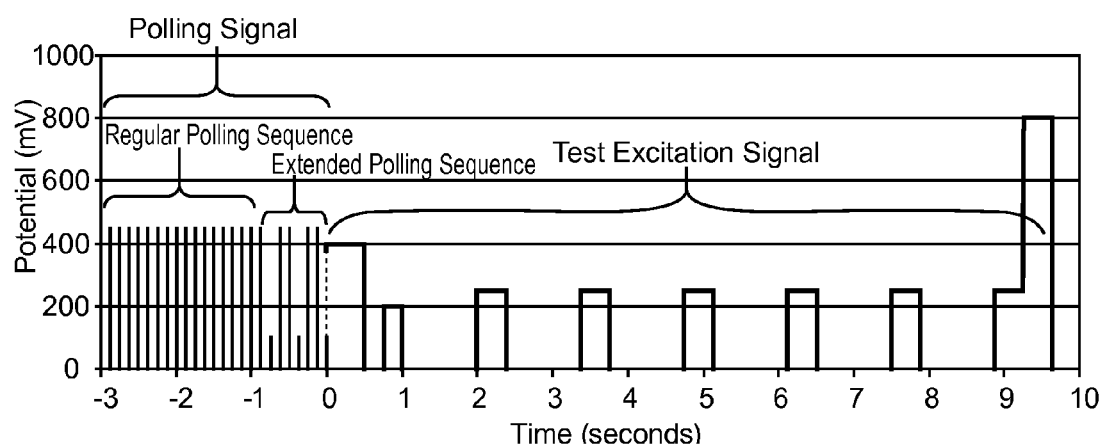

FIG. 3C and FIG. 3D illustrate the regular and extended polling sequences of other polling input signals and other test excitation signals of biosensor systems with a binary underfill management system. In FIG. 3C, the represented polling signal has a regular polling sequence of seven regular input pulses and an extended polling sequence of twenty-one extended input pulses, while in FIG. 3D, the represented polling signal has a regular polling sequence of fifteen regular input pulses and an extended polling sequence of seven extended input pulses. The extended polling sequences have multiple cycles (seven are depicted in FIG. 3C, while three are depicted in FIG. 3D) of extended input pulses with two higher and one lower extended amplitudes. Each cycle has a start cycle pulse, a middle cycle pulse, and an end cycle pulse. The start and middle cycle pulses are similar extended input pulses having amplitudes of about 450 mV, which is essentially the same as the regular amplitude of the regular input pulses. The end cycle pulse is a different extended input pulse with an amplitude of about 100 mV, which is different than the regular amplitudes of the regular input pulses. The pulse widths and relaxation widths of the regular and extended polling signals are essentially the same. While FIG. 3C and FIG. 3D illustrate regular polling sequences followed by extended polling sequences with seven or three cycles, respectively, the regular polling sequence may be implemented after each cycle or after multiple cycles of the extended polling sequence. In FIG. 3C and FIG. 3D, the regular polling sequences detect the presence of the sample while the extended polling sequences detect the fill state. Thus, the number of extended input pulses varies depending on how soon the initially underfilled test sensor is subsequently filled to SFF.

The analytic potential sequence represented in FIG. 3C and in FIG. 3D have seven or eight analytic pulses, respectively, having various pulse widths from about 0.25 sec to about 0.5 sec and various relaxation widths from about 0.25 sec to about 1 sec. The first analytic pulse has an analytic pulse potential of about 400 mV. The second analytic pulse has an analytic pulse potential of about 200 mV. In FIG. 3C the third through the sixth and in FIG. 3D the third through the seventh analytic pulses each have an analytic pulse potential of about 250 mV. In FIG. 3C the seventh analytic pulse and in FIG. 3D the eighth analytic pulse have an analytic pulse potential that varies from about 250 mV to about 600 mV. The first analytic pulse starts essentially at the end of the last extended input pulse in the extended polling sequence for both figures.

In addition to recognizing SFF, underfill, and requesting additional sample, the underfill management system compensates for error in the analysis by adjusting a correlation for determining analyte concentrations in the sample. Preferably the compensation accounts for error associated with variations in the initial and any subsequent fill of the test sensor with sample. Preferably, different compensation systems are used for initially or subsequently SFF test sensors. When the underfill recognition system distinguishes degrees of initial underfill, subsequently SFF test sensors may considered initially HUF or initially LUF. A compensation system for a specific initial fill state can use one or more different compensation equation and different values for each equation. Preferable underfill compensation systems include slope-based compensation for primary compensation paired with optional residual compensation. While these compensation systems are subsequently described, other compensation systems also may used to provide different underfill compensations in response to whether a test sensor is initially or subsequently SFF. Thus, the underfill management system can select between multiple compensation systems in response to the initial and any subsequent fill state determination from the underfill recognition system.

Figure 4A:
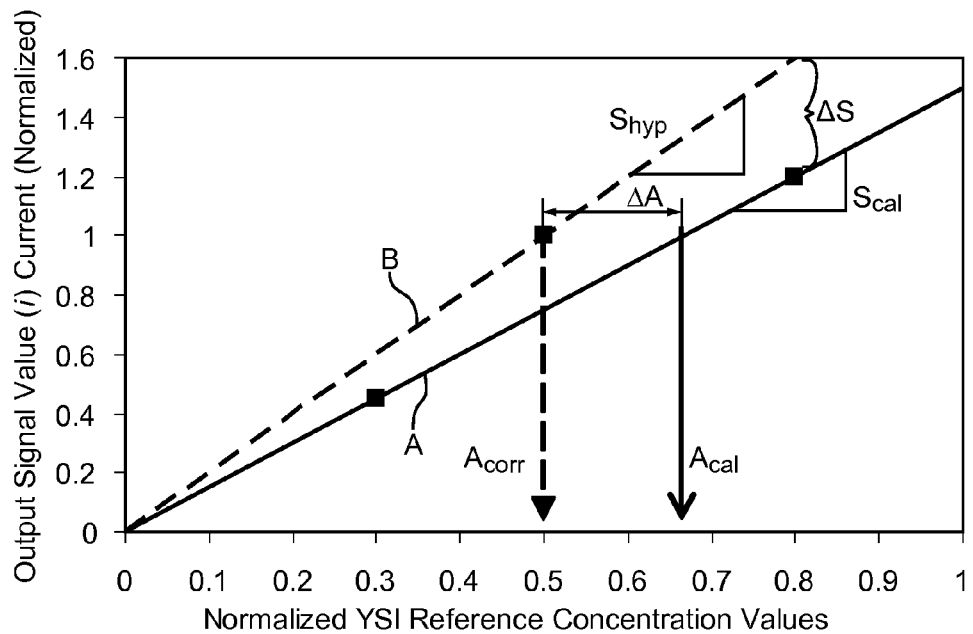
FIG. 4A depicts the relationship between $S_{cal}$, $S_{hyp}$, $\Delta S$, $A_{corr}$, $A_{cal}$, and $\Delta A$.

Slope-based compensation uses predictor functions that compensate for errors in the analyte analysis. Such errors can result in bias, thus reducing the accuracy and/or precision, of the determined analyte concentrations. FIG. 4A pictorially represents a method of slope-based compensation useful for a biosensor system having a linear or near linear relationship between analytic output signals and analyte concentration. The figure shows the relationship between $S_{cal}$, $S_{hyp}$, $\Delta S$, $A_{corr}$, $A_{cal}$, and $\Delta A$. Line A represents a reference correlation having a slope $S_{cal}$ and relating an output signal in the form of current values from a biosensor system to analyte concentration values obtained from a YSI or other reference instrument for the samples. When used during the analysis of a sample by a biosensor system, the reference correlation of Line A may include analytic output signal current values having one or more errors that may provide an inaccurate and/or imprecise analyte concentration value. Line B represents an error-compensated correlation having a slope $S_{hyp}$ and relating current values obtained from the biosensor system with the sample analyte concentration values as obtained from the reference instrument. The error-compensated correlation has been adjusted or modified to reduce or substantially eliminate the one or more errors. $\Delta S$ is the slope deviation between the $S_{cal}$ and $S_{hyp}$ correlation lines, and may be represented as a difference or by other mathematical operators. $\Delta A$ is the difference between the uncompensated or uncorrected ($A_{cal}$) and error compensated or corrected ($A_{corr}$) determined analyte concentration.

Thus, a slope-based compensation equation using $\Delta S$ may be represented as follows:

$$A_{corr} = \frac{i - Int}{S_{cal} + \Delta S}, \quad \text{(Equation 1)}$$

where $A_{corr}$ is the compensated analyte concentration, i is a value of the output signal from a biosensor system, Int is the intercept from a reference correlation equation, $S_{cal}$ is the slope from the reference correlation equation, and $\Delta S$ represents the deviation in slope between $S_{cal}$ and a hypothetical slope of a line ($S_{hyp}$) for the analytic output signal value that provides an analyte concentration of the sample without error. The Int and $S_{cal}$ values for the reference correlation equation may be implemented as a program number assignment (PNA) table, another look-up table, or the like in the biosensor system. The slope deviation term may be normalized to give $\Delta S/S$ and the compensation equation re-written as follows:

$$A_{corr} = \frac{i - Int}{S_{cal} + (1 + \Delta S/S_{cal})}. \quad \text{(Equation 1A)}$$

Other slope compensation equations including at least one slope deviation value and the analytic output signal may be used. While the equations presented throughout the application and claims may include an "=" sign, the sign is used to represent equivalence, relationship, prediction, or the like.

Without compensation, a specific analytic output signal value will provide a different sample analyte concentration from the $S_{cal}$ reference correlation line than from the $S_{hyp}$ error-compensated line. The $A_{corr}$ value obtained from the $S_{hyp}$ error-compensated line provides a more accurate value of the analyte concentration in the sample. Thus, Equations 1 and 1A translate a current value, $S_{cal}$, and Int into the compensated analyte concentration value $A_{corr}$ using $\Delta S$.

If the value of $\Delta S$ is determined experimentally from samples and substituted into Equations 1 or 1A, the bias in the determined analyte concentrations of those samples will be fully compensated. Alternatively, if $\Delta S$ is substituted with a predictor function, then the ability of the compensation equation to correct bias in the determined analyte concentration will depend on how well the value generated from the predictor function correlates with $\Delta S$. Thus for Equation 1, a predictor function, $f(\text{predictor})$, may be substituted for $\Delta S$, and the equation may be rewritten as follows:

$$A_{corr} = \frac{i - Int}{S_{cal} + \Delta S} \quad \text{(Equation 2)}$$
$$= \frac{i - Int}{S_{cal} + f(\text{predictor})}$$
$$= \frac{i - Int}{S_{cal} + b_1 * f(\text{Index}) + b_0}.$$

While the predictor function, $f(\text{predictor})$, may have the general form of $b_1 * f(\text{Index}) + b_0$, other values or indices may be used in combination with the index function $f(\text{Index})$ to provide $f(\text{predictor})$. For example, the index function $f(\text{Index})$ could be used with or without one or both of the $b_1$ (representing slope) and $b_0$ (representing intercept) values to provide the predictor function. Thus, when $b_1=1$ and $b_0=0$, $f(\text{predictor})=f(\text{index})$. Multiple index functions also may be combined to provide the $f(\text{predictor})$, and thus, the corrected analyte concentration of the sample. A predictor or index function will be better at correcting error in the analysis when the function has a greater correlation with the slope deviation.

Predictor functions include at least one index function, and one or more of the index functions may be complex. An index function is responsive to at least one error parameter. Error parameters may be any value responsive to one or more errors in the output signal. Error parameter values may be determined before, during, or after the analysis. Error parameter may be values from the analysis of the analyte, such as the intermediate signals from an analytic output signal; or from secondary output signals independent of the analytic output signal, such as from thermocouple currents or voltages, additional electrode currents or voltages, and the like. Thus, the error parameters may be extracted directly or indirectly from the output signal of the analysis and/or obtained independently from the analytic output signal. Other error parameters may be determined from these or other analytic or secondary output signals. Any error parameter may be used to form the term or terms that make up the index function, such as those described in Intl. Pub. No. WO 2009/108239, filed Dec. 6, 2008, entitled "Slope-Based Compensation," and the like. A more detailed treatment of error correction using index functions and slope deviation values also may be found in this publication.

A calculated number is generated from an index function that correlates with an error parameter, such as hematocrit or temperature, and represents the influence of this error parameter on bias. Index functions may be experimentally determined as a regression or other equation of the plot between the deviation from a reference slope and the error parameter. Thus, the index function represents the influence of the error parameter on the slope deviation, normalized slope deviation, or percent bias. In normalization, the slope deviation, index function, or other parameter is adjusted (multiplied, divided, or the like) by a variable to reduce the statistical effect of changes in the parameter, improve the differentiation in variations of the parameter, standardize measurements of the parameter, a combination thereof, or the like. Index functions, in addition to reference correlation equations, may be predetermined and stored in the biosensor system.

An index function is complex when the index function includes at least two terms, each modified by weighing coefficients. Thus, the weighing coefficients of the complex index functions provide the ability to address the relative significance of multiple error parameters in response to the amount of error each error parameter contributes to the determined analyte concentration. The combination is preferably a linear combination, but other combination methods may be used that provide weighing coefficients for the terms. Each term may include one or more error parameters. A more detailed treatment of using predictor and complex index functions for analyte analysis may be found in Intl. App. No. PCT/US2009/067150, filed Dec. 8, 2009, entitled "Complex Index Functions".

An example of a complex index function is represented as follows:

$$f(CIndex)=a_1+(a_2)(Hct)+(a_3)(R4/3)+(a_4)(R5/4)+(a_5)(R6/5)+(a_6)(R6/4)+(a_7)(Hct)(G_{raw})+(a_8)(R4/3)(G_{raw})+(a_9)(R5/3)(G_{raw})+(a_{10})(R6/5)(G_{raw})+(a_{11})(R6/4)(G_{raw})+(a_{12})(Temp)(Hct)+(a_{13})(Temp)(R5/3)+(a_{14})(Temp)(R6/5)+(a_{15})(Hct)(R5/4)+(a_{16})(Hct)(R6/5)+(a_{17})(Hct)(R6/4)+\ldots, \quad \text{(Equation 3)},$$

where $a_1$ is a constant, $a_2$-$a_{17}$ independently are weighing coefficients, $G_{raw}$ is the determined analyte concentration of the sample without compensation, Temp is temperature, and Hct is the current from an additional electrode. Each of the weighing coefficients ($a_2$-$a_{17}$) is followed by its associated term.

There are at least three basic types of terms in this complex index function: (1) the individual ratio indices extracted from the analytic output signal, such as R3/2 and R4/3, (2) the interaction terms between the ratio indices extracted from the analytic output signal and the temperature, Hct current, and/or $G_{raw}$, such as (Temp)(R5/3) and (R4/3)($G_{raw}$), and (3) temperature, Hct, or $G_{raw}$. The terms may include values other than error parameters, including $G_{raw}$. The complex index function generates a complex index value when the terms are replaced with the appropriate values. Statistical processing may be performed on the multiple terms to determine one or more constants and weighing coefficients. Statistical package software, including MINITAB (MINTAB, INC., State College, Pa.), may be used to perform the statistical processing.

The terms for inclusion in the complex index function may be selected using one or more mathematical techniques to determine exclusion values for each potential term. One or more exclusion tests are then applied to the exclusion values to identify terms to exclude from the complex index function. For example, p-values may be used as part of an exclusion test. The constant $a_1$ may be determined by regression or other mathematical technique. While a single constant is shown in the complex index function, a constant is not required; more than one may be used, and may be equal to 0. Thus, one or more constants may or may not be included in the complex index function. One or more constants also may be combined with the complex index function in forming a predictor function, such as a $b_0$ constant as subsequently described, for example.

A complex index function includes at least two terms that are modified by weighing coefficients. Weighing coefficients are numerical values other than one or zero. Preferably, each term including an error parameter is modified by a weighing coefficient. More preferably, each non-constant term of the complex index function is modified by a weighing coefficient. Weighing coefficients may have positive or negative values. Weighing coefficients may be determined through the statistical processing of the experimental data collected from a combination of multiple analyte concentrations, different hematocrit levels, different temperatures, and the like.

These slope-based and other compensation methods may be paired with residual compensation to further improve the measurement performance of the biosensor system. By focusing on the residual errors and finding residual functions associated with the residual errors, the total error in the analysis may be reduced. The errors from the biosensor system may have multiple error sources or contributors arising from different processes/behaviors that are partially or wholly independent. By compensating primary errors, such as temperature and hematocrit, with a primary compensation function to remove at least 50% of the total error, the remaining residual errors may be determined, and a residual function associated with these residual errors may be determined. A more detailed discussion of residual error compensation may be found in Intl. App. No. PCT/US2011/029318, filed Mar. 22, 2011, entitled "Residual Compensation Including Underfill Error".

Residual error compensation may substantially compensate for the total errors in an analysis until the errors become random. Random errors are those that are not attributed to any error contributor and not described by a residual function at a level considered to be statistically significant. Compensation from primary and residual functions in combination may improve the measurement performance of the biosensor system in more than one way. For example, the combined primary and residual compensation may improve the measurement performance of the biosensor system with regard to a percent bias limit or a percent bias standard deviation, for example.

Residual error compensation may provide the greatest benefit to samples analyzed by users themselves during "self-testing". Residual error compensation also may provide benefit to samples analyzed by a health care professional (HCP). While not wishing to be bound by any particular theory, it is believed that self-testing errors can originate from different behaviors or processes that are substantially independent of controlled environment or HCP-testing errors.

Figure 4B:
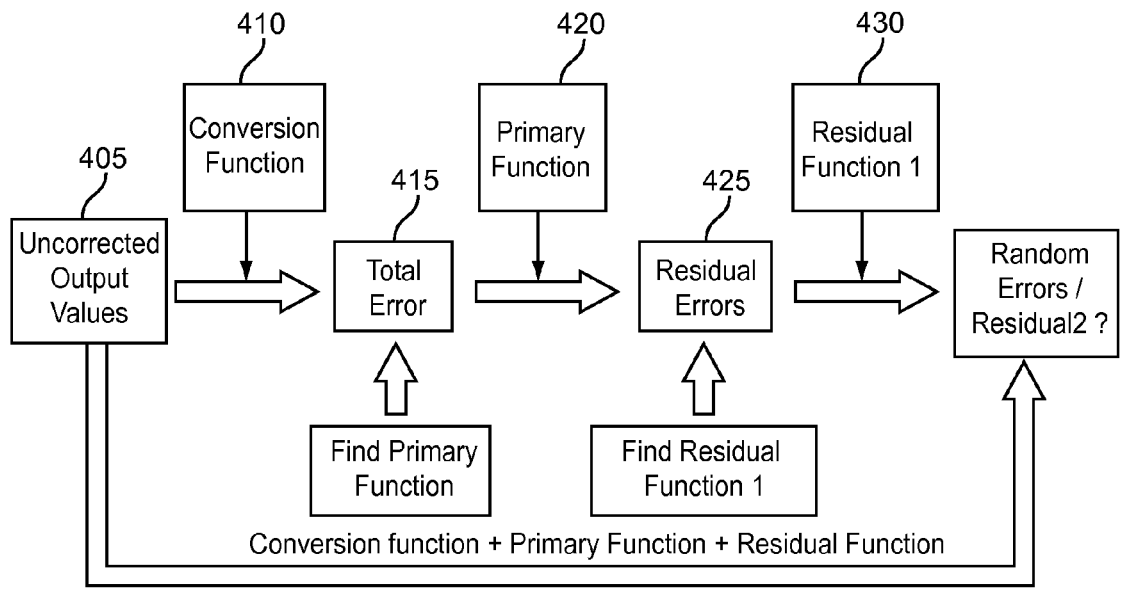
FIG. 4B represents a method of underfill compensation including a conversion function, a primary compensation, and a residual compensation.

FIG. 4B represents the method of error compensation including a conversion function 410, primary compensation, and residual compensation. The output from the conversion function 410 including total error 415 is compensated with a primary compensation in the form of a primary function 420. The remaining residual errors 425 are compensated with a residual compensation in the form of at least a first residual function 430. The total error 415 includes primary and residual errors. The total error 415 also may include random and/or other types of errors. The conversion function 410, the primary function 420, and the first residual function 430, may be implemented as three separate mathematical equations, a single mathematical equation, or otherwise. For example, the conversion function 410 may be implemented as a first mathematical equation and the primary function 420 and the first residual function 430 combined and implemented as a second mathematical equation.

In FIG. 4B, uncorrected output values 405 may be output currents responsive to amperometric, voltammetric, coulometric, or other input signals generating an output signal having a current component. The output signal is responsive to a measurable species in the sample. The measurable species may be the analyte of interest or a mediator whose concentration in the sample is responsive to that of the analyte of interest.

The conversion function 410 is preferably a correlation relationship between the uncorrected output values 405 generated from a sample in response to an input signal from a measurement device and one or more reference analyte concentrations determined at known physical characteristics and environmental aspects of the sample. For example, the sample may be a whole blood sample having a known hematocrit content of 42% where the analysis is performed at a known constant temperature of 25° C. The correlation relationship between known sample analyte concentrations and uncorrected output signal values may be represented graphically, mathematically, a combination thereof, or the like. Correlation relationships may be represented by a program number (PNA) table, another look-up table, or the like that is predetermined and stored in the measurement device.

The primary function 420 providing the primary compensation may include a slope-based function, a complex index function, or other compensation function focusing on the reduction of errors, such as temperature and hematocrit, in the analysis. For example, the observed total error of a biosensor system including a measurement device and a test sensor may be expressed in terms of ΔS/S (normalized slope deviation) or ΔG/G (relative glucose errors). The primary function 420 may compensate at least 50% and preferably at least 60% of the total error 415. The analysis error remaining in the analyte concentration not compensated by the primary function may be considered to arise from operating condition, manufacturing variation, and/or random errors. As the primary function 420 is a function, it may be represented mathematically, such as with an equation, or by a look-up table that is predetermined and stored in the measurement device. The conversion function 410 may be mathematically combined with the primary function 420 to provide a combined equation or look-up table. Suitable primary compensation techniques are described previously and may include additional detail found in Intl. Pub. No. WO 2009/108239, entitled "Slope-Based Compensation" and Intl. App. No. PCT/US2009/067150, entitled "Complex Index Functions", for example. Other primary functions may be used.

When the sample is whole blood and the analyte is glucose, the compensation provided by the primary function 420 may be substantially limited to compensation for analysis errors arising from temperature and hematocrit. Thus, by characterizing the biosensor system with respect to temperature and hematocrit change, the effects from temperature and hematocrit may be compensated by the primary function 420. Other error sources independent of temperature and hematocrit, such as the operating conditions of the system, are preferably not characterized and thus not included in the primary function 420.

The first residual function 430 providing at least a portion of the residual compensation is applied in addition to compensating the primary errors with the primary function 420. Residual errors from error contributors other than temperature and hematocrit may be identified and correlated with one or more index functions. The difference in error between analyses performed in a controlled environment or by a HCP and user self-testing may be expressed generally by Residual Errors=total non-random errors observed−primary function values. Thus, the residual error may be thought of as the non-random error and the manufacturing variation error minus the error projected to be compensated by the primary compensation, such as by the primary function.

The observed residual errors substantially lack the errors removed from the total error by the values of the primary function 420. The total error includes errors from substantially different sources and/or test cases, such as temperature and hematocrit error determined in a controlled environment (substantially described by the primary function), versus operating condition errors originating from outside of a controlled environment (substantially described by the residual function) and manufacturing variation. The first residual function 430 may compensate at least 5%, preferably at least 10%, and more preferably at least 20% of the total error 415. Together, the primary function 420 and the first residual function 430 may compensate at least 60%, and preferably at least 70% of the total error 415.

Residual errors remaining after application of the first residual function 430 may be further reduced if a second residual function is applied. While the errors described by a second residual function may be from either a controlled environment or a non-controlled environment, the errors are preferably non-random errors remaining after primary compensation and/or errors remaining after primary and first residual function compensation. For example, the second residual function may be selected to compensate errors arising at extreme temperature and/or sample hematocrit levels, such at 5° C. and 70% Hct. Thus, the second residual function may be selected to compensate for errors outside of the normal condition range of the primary or the primary and first residual functions. The second residual function also may be selected to compensate systematic deficiencies in the compensation provided by the primary or primary and first residual functions. Additional information regarding second residual functions may be found in Intl. App. No. PCT/US2011/029318, entitled "Residual Compensation Including Underfill Error".

In addition to including primary compensation and at least one residual compensation, the method of error compensation represented in FIG. 4B may include the ability to adjust the compensation provided by the primary compensation in relation to the compensation provided by the residual compensation. The residual compensation also may include the ability to adjust the compensation provided by the first and second residual functions when more than one residual function is used. The error compensation provided by the primary compensation in relation to the compensation provided by the residual compensation may be adjusted because the function or functions making up the residual compensation may be taken from predetermined values stored in the measurement device as a database or otherwise for a limited temperature and/or hematocrit range, while the primary function may be determined from a full range of temperatures and hematocrits. Thus, the primary function may be determined from inputs acquired during the analysis of a sample, while a finite number of residual functions may be predetermined and stored in the measurement device. The error compensation provided by the primary compensation in relation to the compensation provided by the residual compensation also may be adjusted because some overlap may occur between the error described by the primary and one or more residual functions. There may be other reasons to adjust the error compensation provided by the primary compensation in relation to the compensation provided by the residual compensation.

Compensation in a general form where the error compensation provided by the primary compensation is adjusted in relation to the compensation provided by the residual compensation may be expressed as: Primary function+WC*Residual function, where WC is the residual weighing coefficient. The residual weighing coefficient WC may be selected as a function of temperature and/or hematocrit for varying compensation contributions from the residual function. Similarly, compensation including one or more residual functions where the residual functions are each modified by a residual weighing coefficient may take the following general forms:

$$\text{Compensated analyte concentration} = \text{current nA}/(\text{Slope}_{Cal}*(1+\text{primary function}+WC1*\text{residual1}+WC2*\text{residual2}\ldots)), \quad \text{(Equation 4)}$$

or using the alternative general form of residual:

$$\text{Compensated analyte concentration} = \text{current nA}/(\text{Slope}_{cal}*(1+\text{primary function})*(1+WC1*\text{residual1})*(1+WC2*\text{residual2})\ldots), \quad \text{(Equation 5)}$$

where WC1 and WC2 are residual weighing coefficients having values between 0 and 1 and allow the effect of the residual function to be reduced or eliminated when conditions are outside those that were used to develop the residual function. Residual1 is the first level of residual compensation after the primary compensation function, while Residual2 is the next level of residual compensation, but may not be available if an error source/index function is not found. Residual1 and Residual2 are preferably independent of each other and of the primary function.

Weighing coefficients for the primary versus residual compensation and/or for one or more residual functions may be predetermined and stored in the measurement device in the form of a table or through other means. For example, the WC1 and WC2 values may be characterized in a two-dimensional table as a function of temperature and hematocrit. In this way, the weighing coefficient table may be structured to improve the measurement performance of the biosensor system by reducing the effect of the residual function or functions on the determined analyte concentration when the hematocrit content of the sample and the temperature at which the analysis is performed are relatively close to the conditions under which the data was obtained that was used to determine the conversion function 410.

Figure 5A:
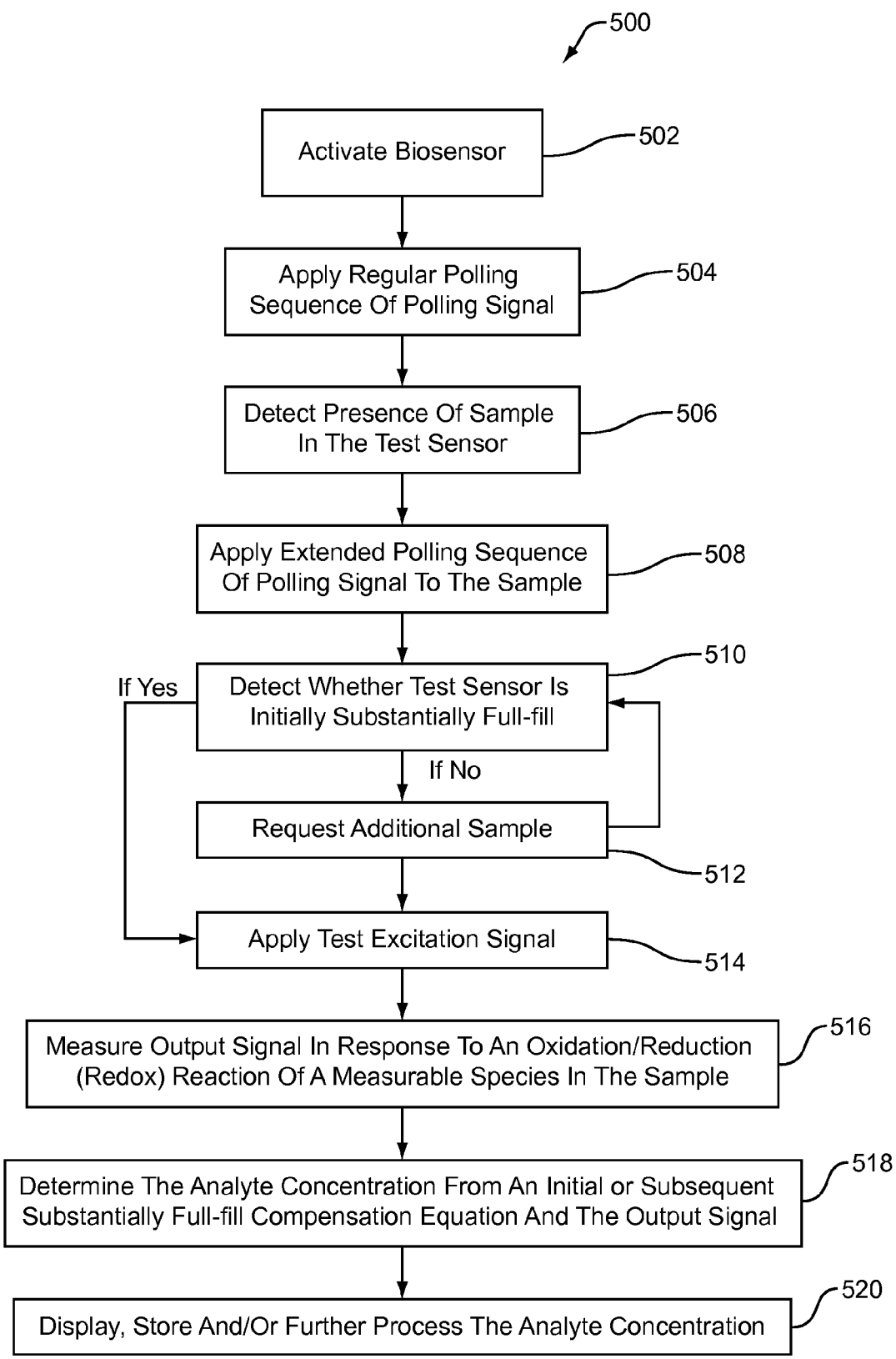
FIG. 5A represents an analysis method for determining an analyte concentration in a sample with a binary underfill management system.

FIG. 5A represents an analysis method 500 for determining an analyte concentration in a sample with a binary underfill management system. In 502, the biosensor system is activated. In 504, the biosensor system applies a regular polling sequence of a polling signal to the sample. In 506, the biosensor system detects the presence of the sample in the test sensor. In 508, the biosensor system applies an extended polling sequence of the polling signal to the sample. In 510, the underfill recognition system detects whether the test sensor is initially SFF. If YES, the underfill management system proceeds to 514, if NO, the underfill management system proceeds to 512. In 512, the biosensor system requests additional sample and returns to 510 to detect whether the test sensor is SFF. While not depicted, if the test sensor remains underfilled, 512 may be repeated. In 514, the biosensor applies a test excitation signal to the sample. In 516, the biosensor measures an output signal in response to a redox reaction of a measurable species in the sample. In 518, the underfill corrected analyte concentration of the sample is determined from an initially or subsequently SFF compensation equation and the output signal. In 520, the analyte concentration may be displayed, stored for future reference, and/or used for additional calculations.

In 502 of FIG. 5A, the biosensor system is activated. The system may be activated by a power switch or button, a sensing mechanism that determines when the measurement device is touched or held by a user, another mechanism that determines when a test sensor is placed within the measurement device, or the like. After activation, the biosensor essentially is ready to receive a sample and to determine the concentration of one or more analytes in the sample.

In 504 of FIG. 5A, the biosensor applies a regular polling sequence of a polling signal to the sample. There may be one or more regular polling sequences in the polling signal. FIG. 3A and FIG. 3C each show regular polling sequences of a polling signal for a binary underfill management system. Other regular polling sequences and polling signals may be used.

In 506 of FIG. 5A, the biosensor detects when a sample of a biological fluid is available for analysis in the test sensor. When no sample is present, the biosensor continues with the regular polling period, cycles through one or more regular polling periods, starts or restarts a regular polling period, deactivates the biosensor, enters a sleep mode, a combination thereof, or the like. The biosensor detects the presence of the sample when at least one of the regular output pulses reaches a sample threshold, and then applies the extended polling sequence. The biosensor may show the sample output signals on a display and/or may store the sample output signals in a memory device.

In 508 of FIG. 5A, the biosensor applies an extended polling sequence of a polling signal to the sample. The biosensor may apply the extended polling sequence immediately at the end of the regular polling sequence, after a transition period, or at another selected time. Immediately includes little or no time transition from the regular polling sequence to the extended polling sequence. There may be one or more extended polling sequences in a polling signal. FIG. 3A and FIG. 3C show extended polling sequences of a polling signal suitable for use with a binary underfill management system. Other extended polling sequences and polling signals may be used.

In 510 of FIG. 5A, the biosensor system detects whether the test sensor is SFF. If the test sensor is not SFF, the analysis moves to 512. If the test sensor is SFF, the analysis moves to 514. As previously discussed, one or more threshold values may be used to determine if the test sensor is initially SFF. Values other than thresholds from the polling output signal also may be used.

In 512 of FIG. 5A, the biosensor system requests the addition of additional sample. The biosensor generates one or more error signals or other indicators to the user. Indicators on the measurement device or elsewhere may signify that the sample size is not large enough to a user, such as with an icon, flashing light, light-emitting diode, audio sound, text message, or the like. Indicators also may signify that the sample size is not large enough to the biosensor, which may perform some function or action responsive to the insufficient sample size, such as stopping the analysis, restarting the polling signal, deactivating the biosensor, or the like. The biosensor system may generate one or more indicators immediately after detection and/or prior to the analysis of the analyte. The one or more indicators may be shown on a display device and/or retained in a memory device.

In 514 of FIG. 5A, the biosensor system applies an analytic test excitation signal to analyze the measurable species in the sample. The biosensor applies the test excitation signal to the sample. The test excitation signal may be applied immediately after the extended polling sequence of the polling signal. The test excitation signal may be applied within a selected time period after the extended polling sequence of the polling signal. The test excitation signal may be a gated amperometric excitation signal, or another excitation signal.

In 516 of FIG. 5A, the biosensor system measures an analytic output signal in response to a redox reaction of a measurable species responsive to the analyte concentration in the sample. The sample generates one or more analytic output signals in response to the test excitation signal. The biosensor may measure the output signal continuously or intermittently. For example, the biosensor may measure the output signal intermittently during the pulses of a gated amperometric excitation signal, resulting in multiple current values recorded during each pulse. The system may show the output signal on a display and/or may store the output signal or portions of the output signal in a memory device.

In 518 of FIG. 5A, the biosensor system selects the compensation system in response to whether the test sensor was initially SFF or subsequently SFF. The compensation system is selected in response to at least one parameter related to the polling signal. Parameters related to a polling signal may include the time of the regular polling sequence, the time of the extended polling sequence, a current or voltage value of a regular polling output signal, a current or voltage value of an extended polling output signal, and the like. The biosensor system correlates the output signals responsive to the concentration of the analyte in the sample with the concentration of the analyte in the sample and compensates in response to the initial fill state of the test sensor.

While the binary underfill management system of analysis method 500 of FIG. 5A uses polling underfill recognition, the method 500 may be similarly implemented with a sequential detection underfill recognition system as previously described. Instead of applying a polling sequence in 504, a relatively short pulse width voltage would be applied across the electrodes and the output currents measured. Thus, the polling sequences of 504 and 508 would be replaced with relatively short pulse width voltages applied across the consecutive electrodes, and the output currents would be measured to determine which pairs of electrodes contact the sample and optionally the time required for the sample to cross the consecutive electrodes. In 506, the presence of the sample would be detected when the output currents reflect that the sample is contacting the sub-element of the counter and the working electrode. In 510, if the presence of the sample were detected, but sufficient sample contact with the working and counter electrodes is not detected, then the method would move to 512 and request additional sample. If sufficient sample contact with the working and counter electrodes is detected in 510, then the method would move to 514 as the test sensor would be initially SFF. The other portions of the analysis method 500 would be performed similarly to the polling method.

Figure 6A:
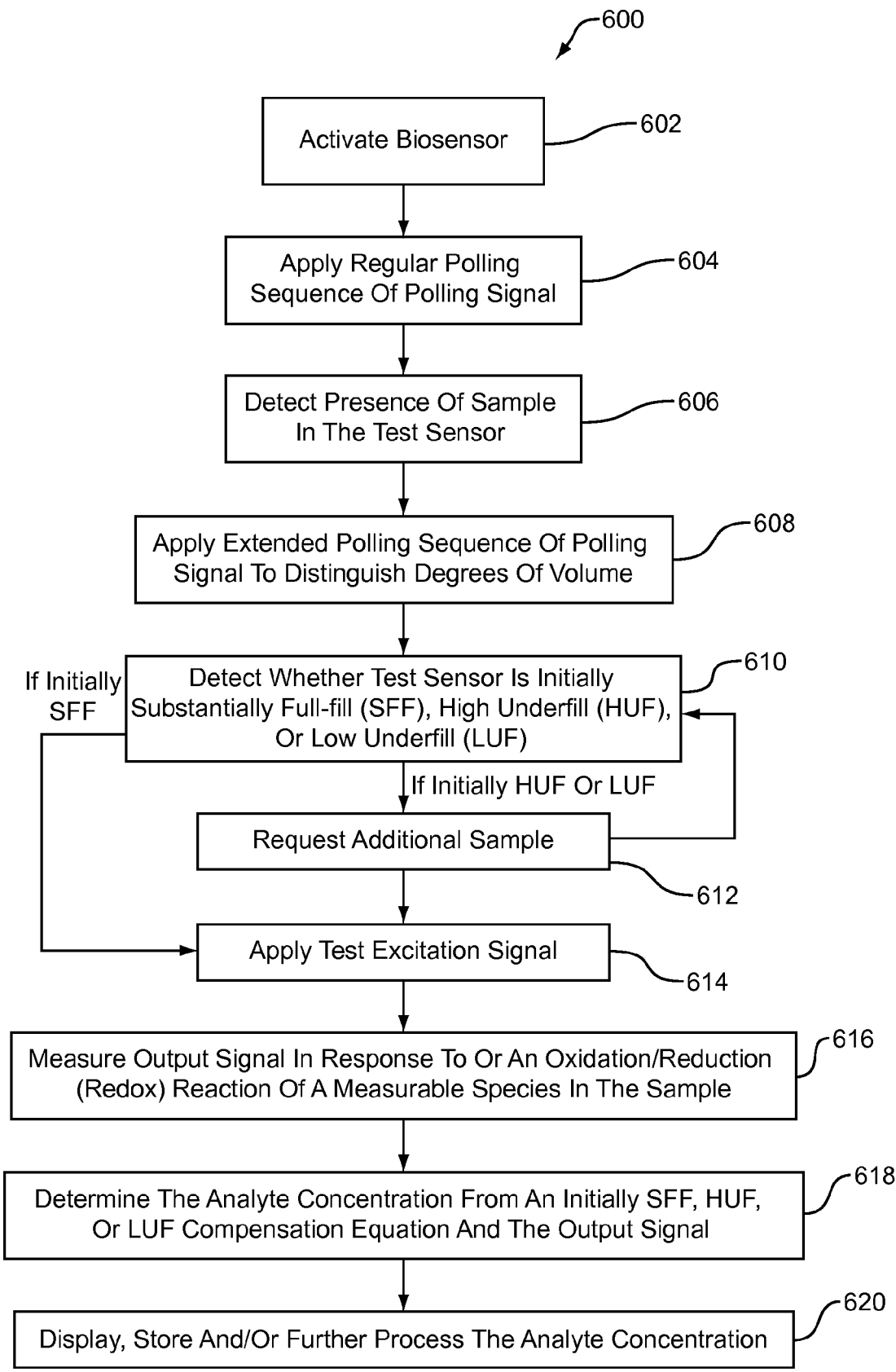
FIG. 6A represents an analysis method for determining an analyte concentration in a sample with an underfill management system that determines the degree of initial underfill.

FIG. 6A represents an analysis method 600 for determining an analyte concentration in a sample with an underfill management system that determines the degree of initial underfill. The method 600 uses polling to recognize the degree of initial underfill. In 602, the biosensor is activated. In 604, the biosensor system applies a regular polling sequence of a polling signal to the sample. In 606, the biosensor system determines the presence of the sample in the test sensor. In 608, the biosensor system applies an extended polling sequence of the polling signal to the sample having the ability to distinguish underfill volumes. In 610, the underfill recognition system detects whether the test sensor is initially SFF, initially HUF, or initially LUF. If initially SFF, the underfill management system proceeds to 614, if initially HUF or LUF, the underfill management system proceeds to 612. In 612, the biosensor system requests additional sample and returns to 610 to determine whether the test sensor is SFF. While not depicted, if the test sensor remains underfilled, 612 may be repeated. In 614, the biosensor applies an analytic test excitation signal to the sample. In 616, the biosensor measures an output signal in response to a redox reaction of a measurable species in the sample. In 618, the compensated analyte concentration of the sample is determined from an initial SFF compensation equation, an initial HUF compensation equation, or an initial LUF compensation equation and the output signal. In 620, the analyte concentration may be displayed, stored for future reference, and/or used for additional calculations.

In FIG. 6A, biosensor activation 602, application of the polling signal 604, sample detection 606, application of the extended polling sequence 608, requesting additional sample 612, and display, storage, and/or further processing of the analyte concentration 620 may be implemented similarly to their counterparts in FIG. 5A. As previously discussed, the extended polling sequence would allow for more than one volume threshold to be met.

In 610 of FIG. 6A, the biosensor system determines if the test sensor is initially SFF, HUF, or LUF. Different threshold values may be used to distinguish between initially SFF, HUF, and LUF states. For example, when the output from the extended polling sequence meets a first threshold value, the test sensor is considered initially LUF. If the extended polling sequence output meets a second threshold value, the test sensor is considered initially HUF. If the extended polling sequence output meets a third threshold value, the test sensor is considered initially SFF. The first, second, and third threshold values are responsive to the fill state of the test sensor. For example, the LUF threshold may be met when from 40% to 50% of the volume of the test sensor is filled, while the HUF threshold is met when from 58% to 70% of the volume of the test sensor is filled. Values other than thresholds from the polling output signal also may be used to determine the initial fill state of the test sensor. Other percentages of test sensor fill may be selected to correspond to the initial fill states of LUF, HUF, and SFF.

In 618 of FIG. 6A, the biosensor system selects the compensation system in response to whether the test sensor was initially SFF, or subsequently filled to SFF after an initial HUF or LUF state. The compensation system is selected by the underfill recognition system in response to at least two parameters related to the polling signal. The underfill management system correlates the output signals responsive to the concentration of the analyte in the sample with the concentration of the analyte in the sample and compensates in response to the initial fill state of the test sensor.

While the underfill management system of analysis method 600 of FIG. 6A uses polling to determine the degree of underfill, the method 600 may be similarly implemented with a sequential detection underfill recognition system as previously described. Thus, the polling sequences of 604 and 608 would be replaced with relatively short pulse width voltages applied across the consecutive electrodes and the output currents measured to determine which pairs of electrodes contact the sample and optionally the time required for the sample to cross the consecutive electrodes. The other portions of the analysis method 600 would be performed similarly to the polling method.

When the test sensor is initially SFF, the underfill management system implements initial SFF compensation. Slope-based compensation equation is preferred for an initial SFF compensation system. An example of an initial SFF slope-based compensation may be represented as follows:

$$A_{comp} = \frac{i - Int}{S_{cal} + f(\text{Index})temp + f(\text{Index})hct}, \quad \text{(Equation 6)}$$

where $f(\text{Index})temp$ is an index function representing the change in slope ($\Delta S$) from the reference correlation attributable to the temperature error parameter, and $f(\text{Index})hct$ is an index function representing the change in slope ($\Delta S$) from the reference correlation attributable to the hematocrit error parameter.

More preferably a slope-based compensation equation is used that includes a complex index function. The complex index function may combine the $f(\text{Index})temp$ and the $f(\text{Index})hct$ index functions into a single mathematical form. An initial SFF slope-based compensation equation including a complex index function with combined temperature and hematocrit functions was previously represented as Equation 3. Most preferably, to also reduce the error introduced by user self-testing for initially SFF test sensors, the underfill management system will implement initial SFF compensation with a slope-based compensation equation including a complex index function as a primary function P1 in addition to first and second residual functions, R1 and R2, respectively. An initial SFF compensation equation including a primary function P1 and first and second residual functions generally may be represented as follows:

$$A_{comp}=i/[S_{cal}*(1+P1+WC_1*R1+WC_2*R2)] \quad \text{(Equation 7)},$$

where $A_{comp}$ is the compensated analyte (such as glucose) concentration of the sample, i is a current value, such as the last current value from the fifth excitation pulse represented in FIG. 2B, $S_{cal}$ is the slope from the reference correlation equation, P1 is the primary function, $WC_1$ is a first residual weighing coefficient, R1 is a first residual function, $WC_2$ is a second residual weighing coefficient, and R2 is a second residual function. While a second residual function is shown, it is not required.

Suitable primary, first and second residual functions, and their associated residual weighting coefficients for use in Equation 7 may be represented as follows:

Primary Function $P1=17.5252-0.012154*'i_{7\text{-}Hct}'-0.0258*'R3/2'-15.057*'R5/4'-20.04*'R6/5'+16.318*'R6/4'-5.1e-7*'i_{7\text{-}Hct}*G_{raw}'+0.0029343*'R4/3*G_{raw}'+0.01512*'R5/4*G_{raw}'-0.0191066*'R6/5*G_{raw}'-1.55e-6*'\text{Temp}*i_{7\text{-}Hct}*R5/4'-0.030154*'\text{Temp}*R5/4'-0.006368*'\text{Temp}*R5/3'-9.476e-4*'i_{7\text{-}Hct}*R4/3'+0.011803*'i_{7\text{-}Hct}*R5/4'+8.112e-4*'i_{7\text{-}Hct}*R5/3'+0.013868*'i_{7\text{-}Hct}*R6/5'-0.01303*'i_{7\text{-}Hct}*R6/4'-9.1e-6*'i_{7\text{-}Hct}*R5/4*G_{raw}'+1.02e-5*'i_{7\text{-}Hct}*R6/5*G_{raw}'$ (Equation 8);

First Residual Function $R1=4.4084+5.683*'R4/3'-5.1348*'R5/4'-4.2282*'R5/3'-7.971*'R6/5'+7.40*'R6/4'+1.08e-5*'i_{7\text{-}Hct}*G_{raw}'-0.0015806*'R32*G_{raw}'-0.018626*'R43*G_{raw}'-0.044513*'R54*G_{raw}'+0.01978*'R53*G_{raw}'+0.04634*'R65*G_{raw}'+0.001481*'\text{Temp}*R32'+0.03006*'\text{Temp}*R54'-0.03737*'\text{Temp}*R64'-0.001453*'i_{7\text{-}Hct}*R43'+7.836e-4*'i_{7\text{-}Hct}*R53'+6.61e-4*'i_{7\text{-}Hct}*R65'+1.75e-5*'i_{7\text{-}Hct}*R54*G_{raw}'-2.89e-5*'i_{7\text{-}Hct}*R65*G_{raw}'$ (Equation 9);

where $i_{7\text{-}Hct}$ is the current from hematocrit sensing electrode at 7 seconds as represented in FIG. 2B; Temp is the measurement device temperature; R3/2, R4/3, R5/4, R6/5, R5/3, and R6/4 are examples of inter-pulse ratio terms having the general format of the last current of a later in time pulse divided by the last current of an earlier in time pulse; and $G_{raw}$ is an uncompensated analyte value.

When the test sensor is initially underfilled and then subsequently filled to SFF, a binary underfill management system will implement subsequently SFF compensation. Binary underfill management systems are generally configured to detect initial HUF as opposed to initial LUF states as initial underfill, as the working electrode of the test sensor generally is contacted with sample to indicate sample presence in binary systems. A slope-based compensation is preferred for a subsequent SFF compensation system. An example of a subsequently SFF slope-based compensation may be represented as follows:

$$A_{comp} = \frac{i - Int}{S_{cal} + f(\text{Index})temp + f(\text{Index})hct + f(\text{Index})SubSFF}, \quad \text{(Equation 10)}$$

where $f(\text{Index})\text{SubSFF}$ is an index function representing the change in normalized slope deviation ($\Delta S/S$) from the reference correlation attributable to the error introduced into the analysis by the initial underfill and subsequent SFF of the test sensor.

More preferably, a subsequent SFF compensation system includes a slope-based compensation equation including a complex index function, where a different primary function, P2, is used than for initial SFF compensation. While different residual functions also could be used, a residual function may be less beneficial than for the initial SFF state as the errors attributable to self-testing are likely changed or reduced by the subsequent fill. Thus, while different residual functions are preferred for each fill state determined by the underfill recognition system, they are not required.

The rational for selection of a different primary function P2 for subsequent SFF compensation is described below with regard to the initial HUF compensation system. In the event that the binary underfill recognition system determines underfill without the sample substantially contacting the working electrode, an initial LUF type compensation system could be used for subsequently SFF compensation. A subsequent SFF compensation equation having a different primary function P2 for use with a binary underfill recognition system that detects initial HUF type underfill may be represented as follows:

Different Primary Function $P2=0.602-0.28941*'R3/2'-22.651*'6/4'-9.204*'R7/6'+22.807*'R7/5'-26.617*'R8/7'+15.771*'R8/6'-0.019103*'R4/3*G_{raw}'+0.018181*'R5/3*G_{raw}'-0.009982*'R6/4*G_{raw}'+0.033009*'R8/7*G_{raw}'-0.022485*'R8/6*G_{raw}'+0.012486*'R3/2*\text{Temp}'+0.939*'R6/4*\text{Temp}'-0.9769*'R7/5*\text{Temp}'+0.56133*'R4/3*EPF_{WE}'-1.1673*'R5/4*EPF_{WE}'+0.57756*'R7/6*EPF_{WE}'-0.002448*'R4/3*G_{raw}*EPF_{WE}'+0.005993*'R5/4*G_{raw}*EPF_{WE}'+0.009662*'R6/5*G_{raw}*EPF_{WE}'-0.0013429*'R6/4*G_{raw}*EPF_{WE}'-0.011844*'R7/6*G_{raw}*EPF_{WE}'$ (Equation 10A), where $EPF_{WE}$ is an extended polling factor representing an underfill condition where the working electrode is significantly contacted by the sample. In the case of a sequential detection underfill recognition system, a sequential detection factor ($SDF_{WE}$), could be used for the $EPF_{WE}$.

FIG. 7A, FIG. 7B, FIG. 7C, and FIG. 7D depict comparisons between uncompensated and compensated glucose analyte concentrations determined from whole blood samples including red blood cells when the test sensors were initially underfilled and subsequently SFF with whole blood. The test sensors were initially filled with a sample volume below 0.5 microliters to create underfilled test sensors, where 0.5 microliters was the SFF volume for the sample reservoir of the test sensors. Additional sample was added to the underfilled test sensors to provide subsequent SFF test sensors, and the glucose concentration of each sample was then determined. These readings also were compared with readings from sensors that were initially SFF.

Figure 7A:
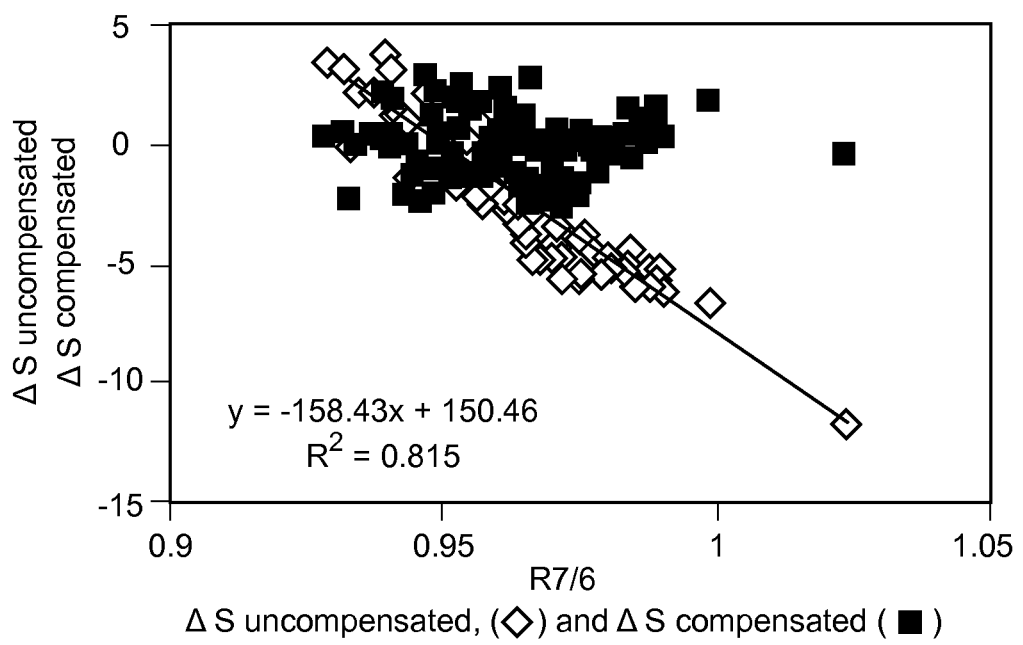
FIG. 7A depicts correlations between $\Delta S$ values before ($\Delta S_{uncomp}$) and after ($\Delta S_{comp}$) compensation with a subsequently SFF compensation equation including an index function relating a ratio error parameter (R7/6) to slope.

FIG. 7A depicts correlations between ΔS values before ($\Delta S_{uncomp}$) and after ($\Delta S_{comp}$) compensation with subsequent SFF compensation including an index function relating a ratio error parameter (R7/6) to slope. The ratio error parameter, R7/6, represents the relationship between the analytic output signal currents generated by the measurable species in response to the $6^{th}$ and $7^{th}$ pulses of a gated amperometric test excitation pulse sequence including at least 7 pulses. Other output signal currents and pulse references may be used. The ratio error parameter R7/6 is an example of an error parameter determined from the analytic output signal. The index function relating the ratio error parameter R7/6 to slope may be selected from various index functions that also relate other error parameters to slope.

Figure 7B:
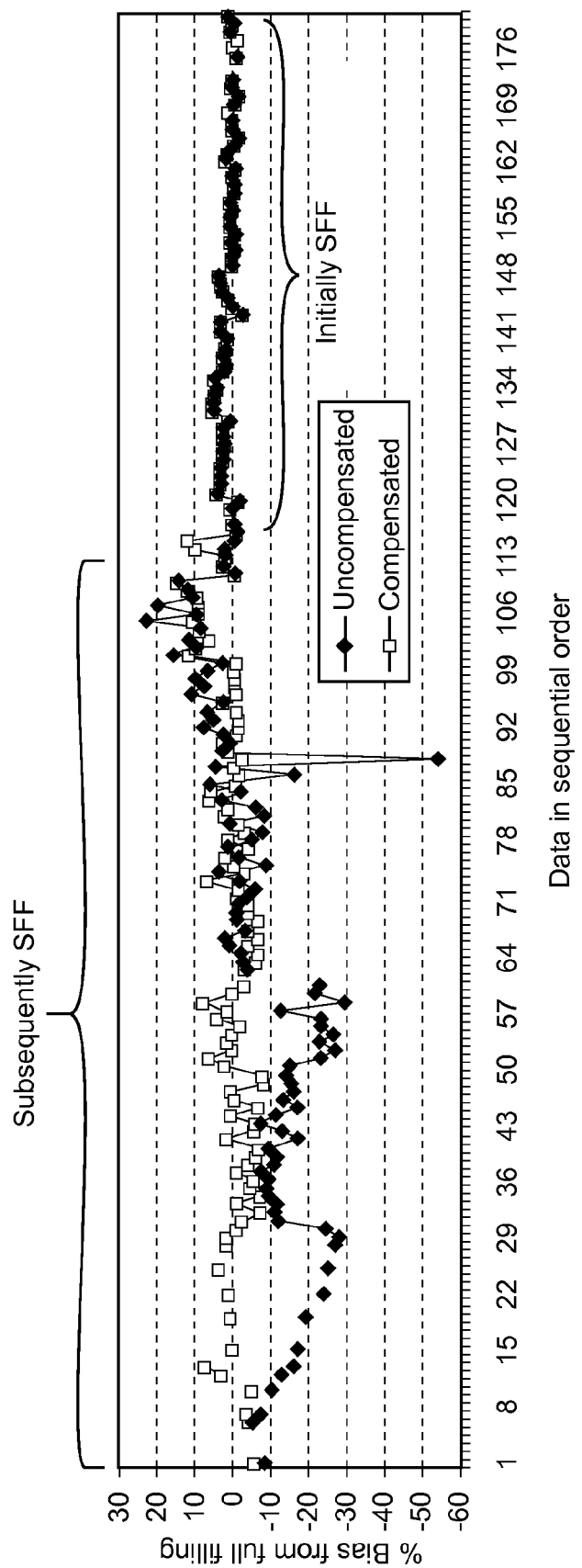
FIG. 7B and FIG. 7D depict the %-Bias values for multiple uncompensated and compensated analyses of subsequently SFF and initially SFF test sensors.

FIG. 7B depicts the %-Bias values for multiple uncompensated and compensated analyses of subsequent SFF test sensors and initially SFF test sensors when the correlation of FIG. 7A was used as an index function in accord with Equation 10. FIG. 7D depicts similar data when the index function relating a ratio error parameter (R7/6) to slope was replaced with the complex index function of Equation 10A was used as a different primary function. The diamond symbols correspond to Bias values for uncompensated subsequent SFF determined analyte concentrations, whereas the square symbols correspond to Bias values for subsequent SFF compensated analyte concentrations. The determined analyte concentrations from test sensors that were initially SFF are identified at the right of the graph. The remaining readings were from initially underfilled test sensors that were subsequently SFF with a second filing prior to analysis.

Figure 7C:
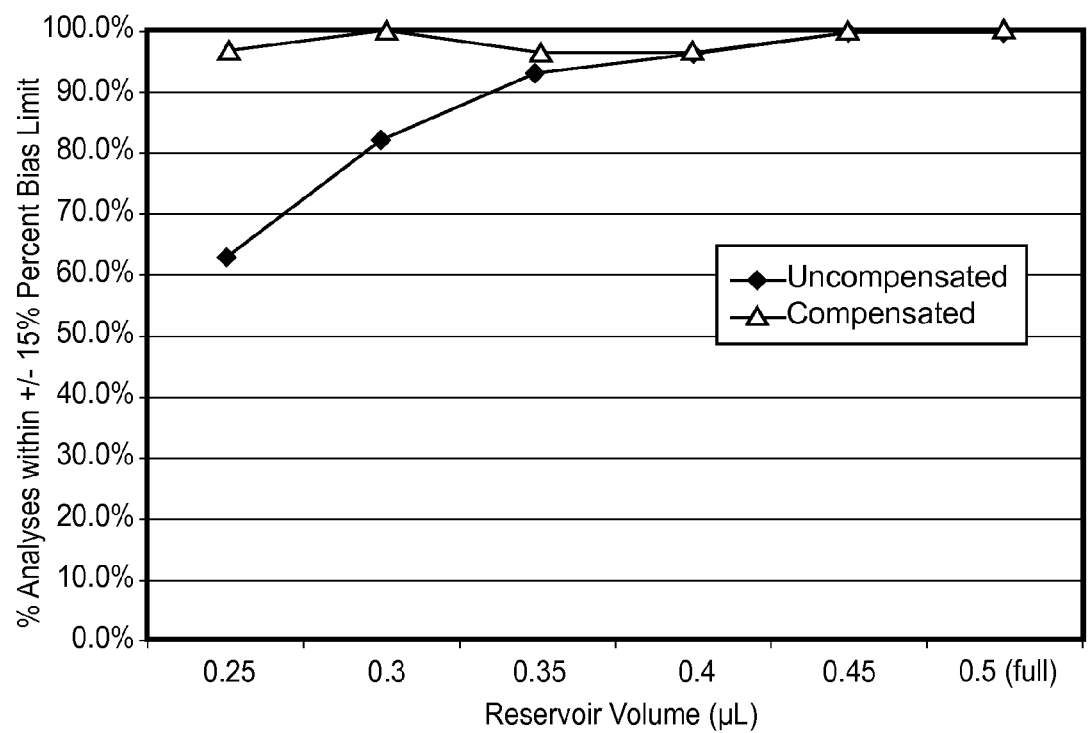
FIG. 7C plots the percent of uncompensated and compensated determined glucose analyte concentrations falling within a ±15% percent bias limit when the test sensors were initially underfilled and subsequently SFF for analysis.
Figure 7D:
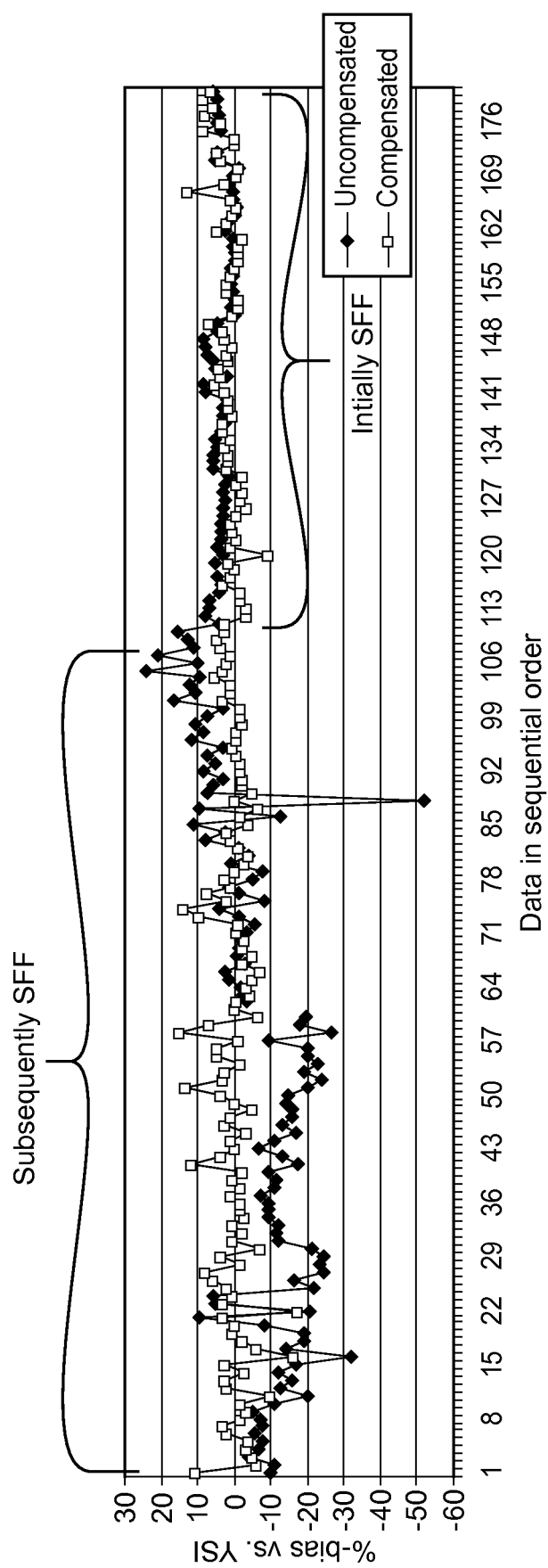

FIG. 7C plots the percent of uncompensated and compensated determined glucose analyte concentrations falling within a ±15% percent bias limit when the test sensors were initially underfilled and subsequently SFF for analysis. The right of the graph shows that initial fills of about 0.4 microliter and greater did not benefit from the subsequent SFF compensation system. Thus, for this underfill management system, the underfill recognition system could be set to consider about 0.4 microliters SFF. The about 0.45 microliter volume also could be selected as SFF as there is no disadvantage to using initial or subsequent SFF compensation systems in the about 0.4 to about 0.45 microliter volume range. The underfill recognition system was configured to recognize a sample size of about 0.25 microliters as present, but initially underfilled.

The darker line of FIG. 7C shows the percentage of determined analyte concentrations falling within the ±15% percent bias limit when the test sensors were initially underfilled, subsequently SFF, but subsequent SFF compensation was not applied. The lighter line shows the percentage of determined analyte concentrations falling within the ±15% percent bias limit when the test sensors were initially underfilled, subsequently SFF, and subsequent SFF compensation was applied. The smaller the initial underfill volume, the greater the improvement provided by subsequent SFF compensation. At the lowest initial underfill volume of about 0.25 microliters, only 63% of the uncompensated glucose readings fell within the ±15% percent bias limit, whereas 96% of the compensated glucose readings fell within the ±15% percent bias limit.

Figure 7E:
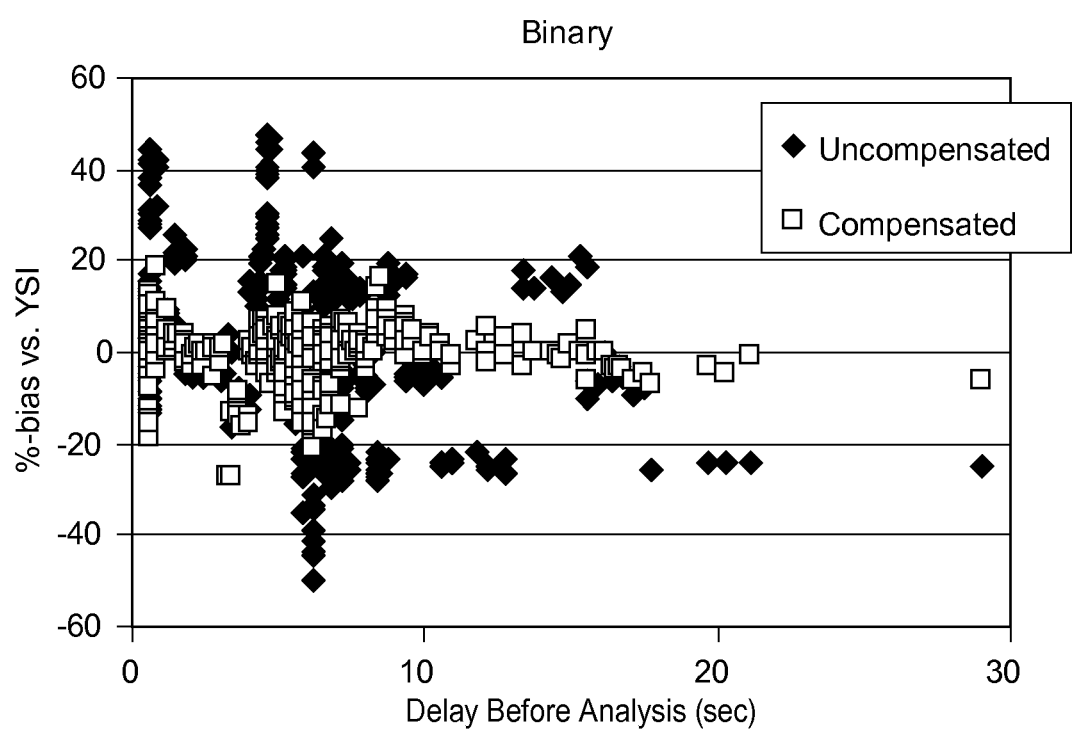
FIG. 7E shows the measurement performance of the binary compensation system with a complex index function.

FIG. 7E shows the measurement performance provided by the binary compensation system when initially underfilled and subsequently SFF test sensors were analyzed and the subsequent fill followed the initial fill by up to approximately 30 seconds. The X-axis of the graph shows the time delay between the initial sample fill of the test sensor and the subsequent sample fill of the test sensor. Subsequent fill delays from approximately 3 seconds to approximately 30 seconds were used. In this instance, the complex index function of Equation 10 A provided comparable measurement performance to Equation 10 when used with the index function relating a ratio error parameter (R7/6) to slope.

When the test sensor is initially underfilled and then subsequently SFF, an underfill management system capable of determining degrees of initial underfill will implement initial LUF or initial HUF compensation. This ability can improve the measurement performance of the biosensor system, especially with regard to test sensor underfill volumes that show little improvement when compensated with the subsequently SFF compensation system of a binary underfill management system. For example, the volume range from about 0.35 to about 0.42 microliter of the test sensor described with regard to FIG. 7C could benefit from a different underfill compensation system than that used for the about 0.25 to about 0.35 underfill volumes. While two degrees of initial underfill, LUF and HUF, are described below, other degrees of initial underfill may be determined and managed by the underfill management system.

An initial LUF compensation system preferably includes the same primary function P1 as used when the test sensor is initially SFF. However, the primary function P1 is preferably paired with at least a different first residual function than used for an initially SFF test sensor. Thus, P1 is preferably used with a different first residual function R3. The initially SFF second residual function may be used, a different second residual function may be used than the initially SFF second residual function, or no second residual function may be used with the initial LUF compensation system.

While a different primary function could be used, the primary function P1 from the initial SFF state is preferred for the initial LUF compensation system because for an initial LUF state the initial sample fill does not substantially react with the reagents of the working electrode. A different first residual function is preferably used in the initial LUF compensation system to account for the substantial effect of self-testing type error on the analysis due to the initial LUF. While not wishing to be bound by any particular theory, an initial LUF state can be thought of as a severe self-testing type error. A preferred initial LUF compensation equation may be represented as follows:

$$A_{comp} = i/[S_{cal}*(1+P1+WC_1*R3)] \quad \text{(Equation 11)},$$

where $A_{comp}$ is the compensated analyte (such as glucose) concentration of the sample, i is a current value, such as the last current value from the fifth excitation pulse represented in FIG. 2B, $S_{cal}$ is the slope from the reference correlation equation, P1 is the primary function previously represented as Equation 8, $WC_1$ is a first residual weighing coefficient, and R3 is a different first residual function. While a different second residual function was not used, one could be included. Preferably, the primary function P1 will compensate for about 90% of the total non-random error in the analysis, while the first different residual function will compensate for the remaining 10% of the non-random error.

A suitable different first residual function R3 for use in Equation 11 may be represented as follows:

$$\begin{aligned}
\text{Different First Residual Function } R3 = & -11.8098 + \\
& 0.0039471*`i_{7\text{-}Hct}`-0.46222*`R2/1`+9.2972*`R4/3`+6.4753*`R5/4`-9.0922*`R5/3`+5.6898*`R6/5`- \\
& 0.00000113*`i_{7\text{-}Hct}*G_{raw}`-0.00034435*`R2/1`*G_{raw}`+0.0024328*`R4/3`*G_{raw}`- \\
& 0.0034962*`R5/3`*G_{raw}`+0.0022624*`R6/5`*G_{raw}`-0.052217*`\text{Temp}*R4/3`+ \\
& 0.046291*`\text{Temp}*R5/3`+0.00024631*`i_{7\text{-}Hct}*R2/1`-0.0057016*`i_{7\text{-}Hct}*R4/3`+0.0056713*`i_{7\text{-}Hct}*R5/3`-0.0041934*`i_{7\text{-}Hct}*R6/4`+ \\
& 0.00000085*`i_{7\text{-}Hct}*R6/5*G_{raw}`+ \\
& 0.0040847*`\text{SDF}*R2/1`+0.025846*`\text{SDF}*R4/3`-0.032782*`\text{SDF}*R5/4` \quad \text{(Equation 12)},
\end{aligned}$$

where SDF is a sequential detection factor representing an underfill condition where the working electrode is not significantly contacted by the sample. In the case of a polling underfill recognition system, an extended polling factor (EPF), could be used for the SDF.

FIG. 8A, FIG. 8B, FIG. 8C, and FIG. 8D show the measurement performance of the LUF compensation system using the primary function of Equation 8 and the different first residual function of Equation 12. About 100 test sensors were initially SFF and the glucose concentrations determined with and without an initial SFF compensation system as previously described. About 600 test sensors were initially filled to a LUF volume, about 0.25 microliters for these test sensors, and subsequently filled to SFF before the glucose concentrations were determined with and without a LUF compensation system. The whole blood samples analyzed for glucose included samples representing a full range of glucose concentrations, hematocrit contents, and analysis temperatures.

Figure 8A:
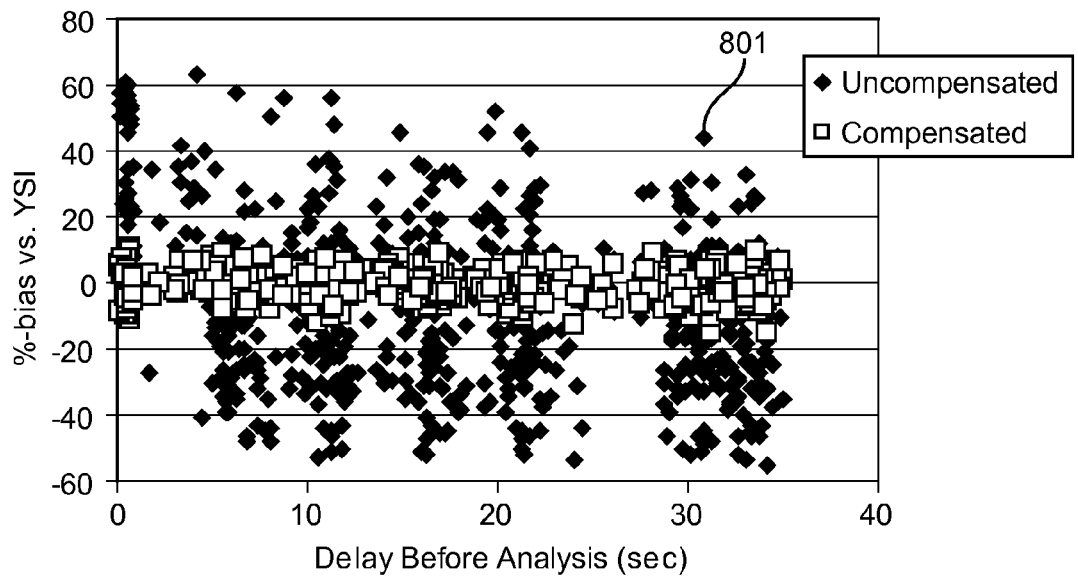
FIG. 8A, FIG. 8B, FIG. 8C, and FIG. 8D show the performance of the LUF compensation system using a primary function and a different first residual function.
Figure 8B:
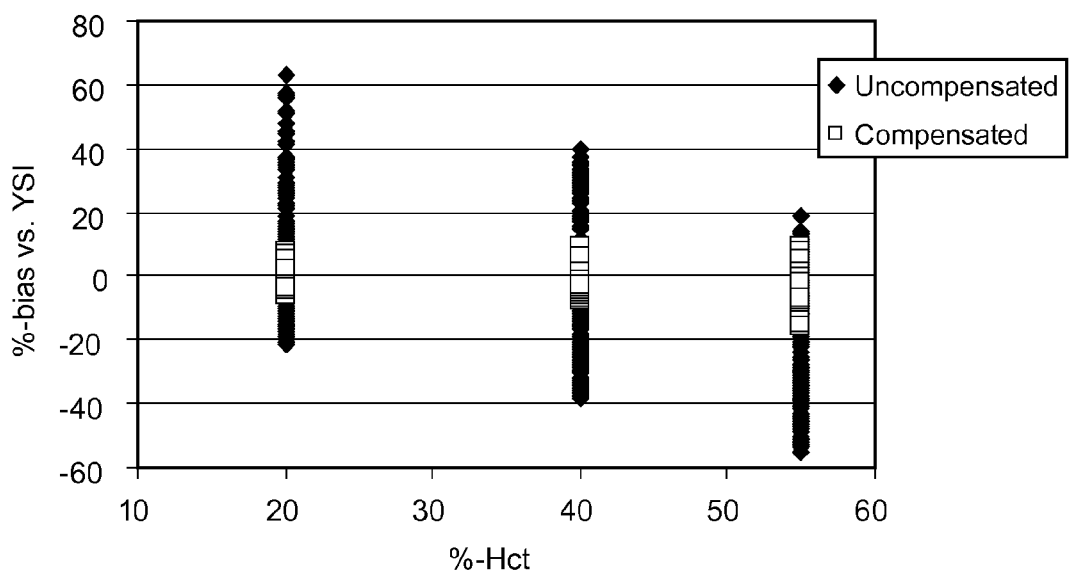
Figure 8C:
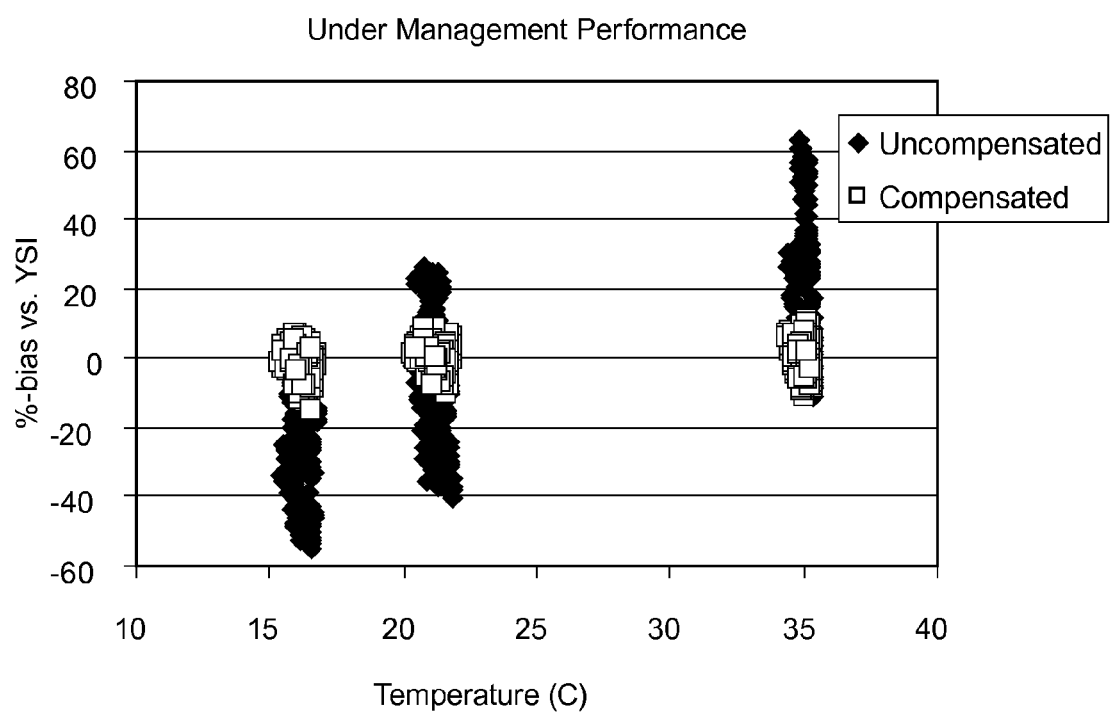
Figure 8D:
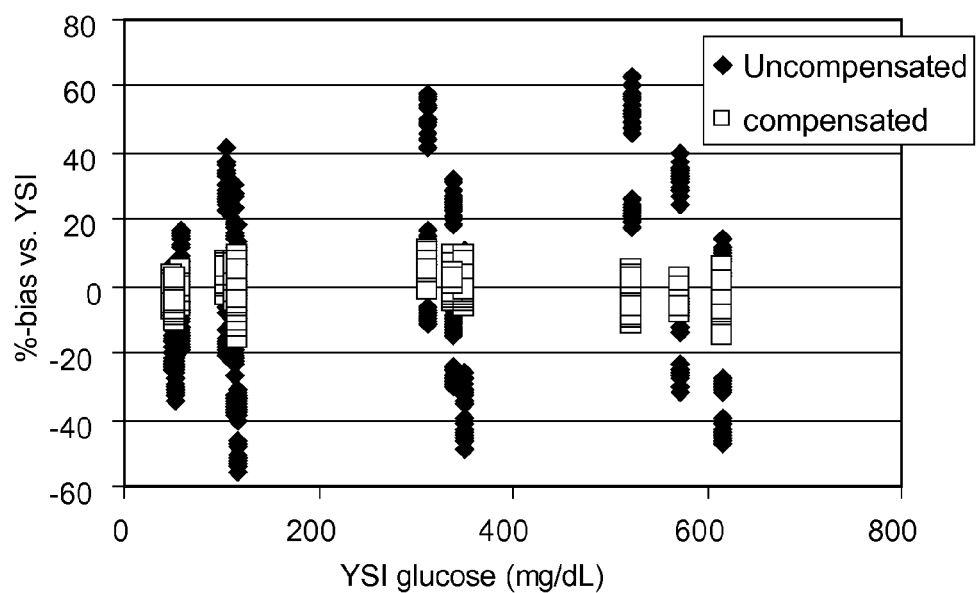

FIG. 8A shows the measurement performance provided by the LUF compensation system when initially LUF and subsequently SFF test sensors were analyzed and the subsequent fill followed the initial fill by up to nearly 40 seconds. The X-axis of the graph shows the time delay between the initial sample fill of the test sensor and the subsequent sample fill of the test sensor. Subsequent fill delays from approximately 3 seconds to approximately 35 seconds were used. For example, analysis 801 is the uncompensated determined glucose concentration from an analysis where the test sensor was initially LUF and subsequently SFF after about 30 seconds had passed since the initial fill. FIG. 8B shows the measurement performance with the LUF compensation system from the data set of FIG. 8A for whole blood samples including a hematocrit content of approximately 20, 40, and 55% (volume/volume). FIG. 8C shows the measurement performance with the LUF compensation system also from the same data set for samples analyzed at approximately 15°, 22°, and 35° C. FIG. 8D shows the measurement performance with the LUF compensation system for samples having glucose concentrations of approximately 50, 75, 330 and 550 mg/dL.

Table I, below, summarizes the measurement performance results for the initially LUF and subsequently SFF test sensors without compensation and with the LUF compensation system. Table I also summarizes the overall performance results for initially SFF test sensors without compensation and with the initial SFF compensation system for comparison. Table I shows the mean percent bias and thus the percent bias standard deviation determined from both the 596 initially LUF and subsequently SFF test sensors and from the 112 initially SFF test sensors. The percent of the analyses falling within a ±5%, a ±8%, a ±10%, a ±12.5%, and a ±15% percent bias limit in relation to the reference glucose concentration of the blood samples as determined with a YSI reference instrument also are shown.

The use of the LUF compensation system with test sensors that were initially LUF and subsequently SFF also provided a percent bias standard deviation of less than 5 for 600 or fewer analyses performed with 600 or fewer test sensors. This represented a greater than 80% (23.05−4.02/23.05*100) improvement in the percent bias standard deviation in relation to the uncompensated analyses.

These measurement performance results were achieved with a LUF compensation system for whole blood samples having an approximately 20% (volume/volume) to approximately 55% hematocrit content, over a sample temperature range from approximately 15° C. to approximately 35° C., and for glucose concentrations over an approximately 50 mg/dL to 500 mg/dL range. The underfill management system provided these results for test sensors initially LUF and subsequently SFF within 6 seconds or less from the initial fill, within 15 seconds or less from the initial fill, within 30 seconds or less from the initial fill, and within 35 seconds or less from the initial fill. Thus, the LUF compensation system provided a significant improvement in measurement performance to the biosensor system for initially LUF test sensors that were subsequently filled to SFF within approximately 40 seconds.

An initial HUF compensation system preferably includes a different primary function P2 than used when the test sensor is initially SFF. The different primary function P2 may optionally be paired with a different first residual function than was used for an initially SFF test sensor. Thus, P2 is used with a different first residual function than was used for the initially SFF test sensor if the initial HUF compensation system includes a first residual function, but a first residual function may not be used with the initial HUF compensation system. The initially SFF second residual function may be used, a different second residual function may be used than the initially SFF second residual function, or no second residual function may be used with the initial HUF compensation system. If a first residual is used with the initial HUF compensation system, the first residual function is different than that for an initial SFF state as the primary function has

TABLE I

|  | Mean %-bias | % Bias SD | %-within ±5% | %-within ±8% | %-within ±10% | %-within ±12.5% | %-within ±15% | Analyses |
|---|---|---|---|---|---|---|---|---|
| Initially LUF Comp | −0.56 | 4.02 | 77.5 | 96.0 | 98.7 | 99.5 | 99.8 | 596 |
| Initially SFF Comp | −0.20 | 4.97 | 77.7 | 89.3 | 94.6 | 99.1 | 99.1 | 112 |
| Initially LUF Un-Comp | −10.26 | 23.05 | 13.6 | 23.3 | 28.7 | 35.7 | 40.4 | 596 |
| Initially SFF Un-Comp | 0.30 | 27.47 | 15.2 | 19.6 | 21.4 | 26.8 | 41.1 | 112 |

For approximately 600 or fewer test sensors, use of the LUF compensation system with test sensors that were initially LUF and subsequently SFF placed greater than 95% of the analysis within a ±10% percent bias limit, greater than 85% of the analysis within a ±8% percent bias limit, and greater than 75% of the analysis within a ±5% percent bias limit. This represented a greater than 240% (98.7−28.7/28.7*100) improvement at the ±10% percent bias limit and a greater than 400% (77.5−13.6/13.6*100) improvement at the ±5% percent bias limit in relation to the uncompensated analyses from initial LUF and subsequently SFF test sensors. In fact, similar or better compensated measurement performance was observed for the initial LUF and subsequently SFF test sensors in relation to initially SFF test sensors.

changed from P1 to P2 and the residual function compensates for error not substantially compensated by the primary function.

A different primary function from the initial SFF state is preferred for an initial HUF state because for a HUF state the initial fill of sample begins chemically reacting with the reagents of working electrode to generate measurable species. Thus, measurable species is generated before and after a subsequent sample fill is provided to the test sensor. This situation may result in more measurable species being present in the sample when the analytic test excitations are applied to the sample when an initial HUF occurs than when an initial SFF occurs. Thus, the initial HUF state may provide a different relationship between the electrochemical redox rate of the measurable species and the underlying analyte concentration of the sample during the analytic portion of the analysis than would exist if the test sensor was initially SFF. Thus, an initial HUF state that is subsequently SFF can be thought of as a substantially different analysis than when an initial SFF test sensor is analyzed.

Although not preferred, an initial HUF compensation system could use the same primary function P1 as was used when the test sensor is initially SFF. In this instance, however, as for the initial LUF compensation system, a different first residual function would be used. In practice, this would likely result in the different first residual function taking over more of the compensation from the primary function P1 than desired as a post-HUF analysis may be thought of as a substantially different analysis than a post-SFF or post-LUF analysis. Thus, use of the initial SFF or LUF primary function with a different first residual function would likely result in the different first residual function compensating for more than 10% of the non-random error in the uncompensated analyte concentration—a situation that would likely work, but is not preferred. Furthermore, this situation results in the different first residual function compensating more for "deficiencies" in the primary function P1 that compensating for errors in the analysis. This would likely result in the first residual function being less effective at compensating errors in the analysis. Thus, while an initial HUF compensation system could use the initial SFF primary function P1 alone or with a different first residual, a different primary function P2, with or without a different first residual function, is preferred for an initial HUF compensation system. A preferred initial HUF compensation equation may be represented as follows:

$$A_{comp} = (i - \text{Int})/[S_{cal}*(1+P2)] \quad \text{(Equation 13)},$$

where $A_{comp}$ is the compensated analyte (such as glucose) concentration of the sample, i is a current value, such as the last current value from the fifth excitation pulse represented in FIG. 2B, Int is the intercept from a reference correlation equation, $S_{cal}$ is the slope from the reference correlation equation, and P2 is a different primary function than previously represented in Equation 8. While a different first residual function was not used as self-testing error has been substantially reduced by the lengthened sample reaction time with the working electrode reagents, one could be included.

A suitable different primary function P2 for use in Equation 13 may be represented as follows:

Different Primary Function $P2 = 8.9398 -$
0.0034873*'$i_{7\text{-}Hct}$'+0.09534*'Temp'+
0.56865*'R1'−0.67442*'R2/1'+1.7684*'R5/3'−
11.9758*'R6/5'−0.00029591*'$i_{7\text{-}Hct}$*R1'+
0.00044337*'$i_{7\text{-}Hct}$*R2/1'+0.0024269*'$i_{7\text{-}Hct}$*R5/4'+0.0051844*'$i_{7\text{-}Hct}$*R6/5'−
0.0038634*'$i_{7\text{-}Hct}$*R6/4'−0.00073925*'R2/1*$G_{raw}$'−0.00188086*'R3/2*$G_{raw}$'−
0.033466*'R4/3*$G_{raw}$'+0.041547*'R5/3*$G_{raw}$'+
0.040176*'R6/5*$G_{raw}$'−0.045438*'R6/4*$G_{raw}$'−
0.061549*'Temp*R4/3'0.31944*'Temp*R5/4'+
0.30496*'Temp*R6/4'−
0.0077184*'$SDF_{WE}$*R1'+
0.0036398*'$SDF_{WE}$*R21'−
0.0018913*'$SDF_{WE}$*R43' (Equation 14), where R1 is an example of an intra-pulse current ratio ($i_{1,5}/i_{1,1}$) term, and $SDF_{WE}$ is a sequential detection factor representing an underfill condition where the working electrode is significantly contacted by the sample.

FIG. 9A, FIG. 9B, FIG. 9C, and FIG. 9D show the performance of the HUF compensation system using the different primary function of Equation 14. About 100 test sensors were initially SFF and the glucose concentrations determined with and without an initial SFF compensation system as previously described. About 650 test sensors were initially filled to a HUF volume, about 0.43 microliters for these test sensors, and subsequently filled to SFF before the glucose concentrations were determined with and without a HUF compensation system. The whole blood samples analyzed for glucose included samples representing a full range of glucose concentrations, hematocrit contents, and analysis temperatures.

Figure 9A:
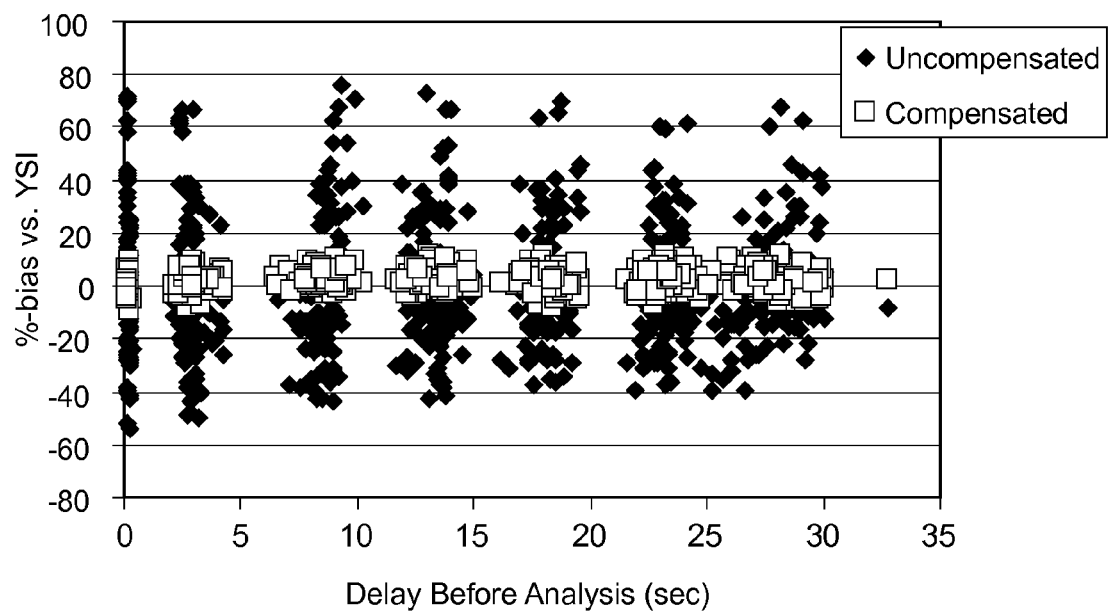
FIG. 9A, FIG. 9B, FIG. 9C, and FIG. 9D show the performance of the HUF compensation system using a different primary function.
Figure 9B:
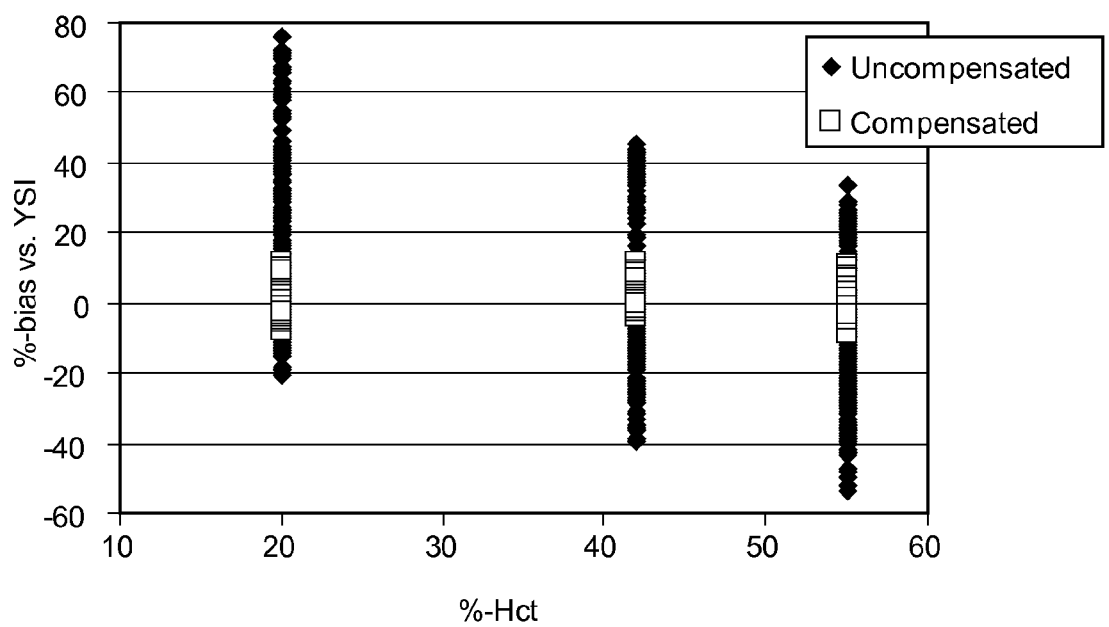
Figure 9C:
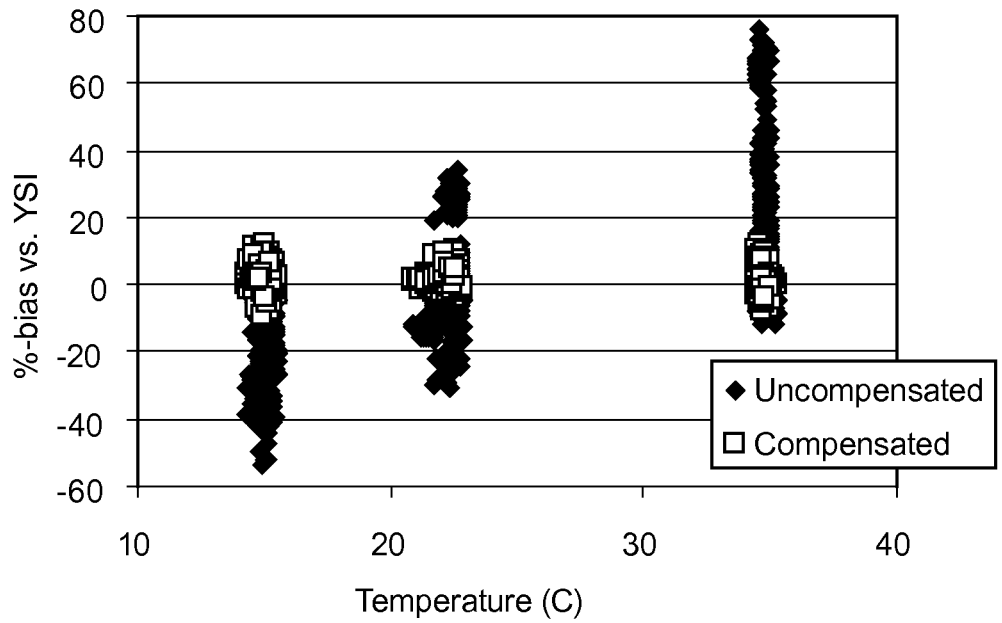
Figure 9D:
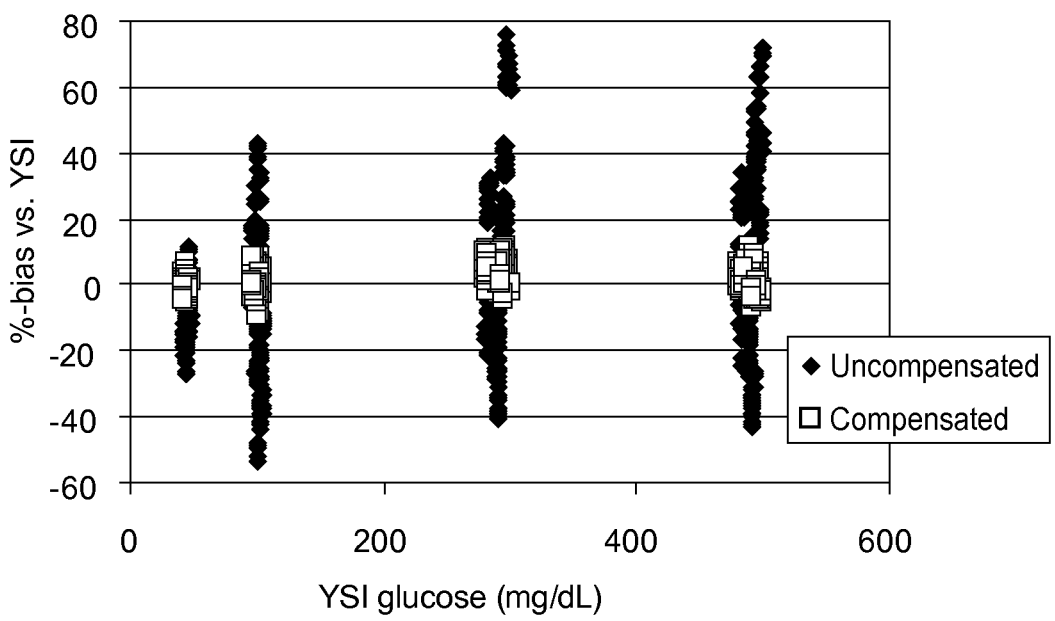

FIG. 9A shows the measurement performance provided by the HUF compensation system when initially HUF and subsequently SFF test sensors were analyzed and the subsequent fill followed the initial fill by up to nearly 40 seconds. The X-axis of the graph shows the time delay between the initial sample fill of the test sensor and the subsequent sample fill of the test sensor. Subsequent fill delays from approximately 3 seconds to approximately 35 seconds were used. FIG. 9B shows the measurement performance with the HUF compensation system from the data set of FIG. 9A for whole blood samples including a hematocrit content of approximately 20, 40, and 55% (volume/volume). FIG. 9C shows the measurement performance with the HUF compensation system also from the same data set for samples analyzed at approximately 15°, 22°, and 35° C. FIG. 9D shows the measurement performance with the HUF compensation system for samples having glucose concentrations of approximately 50, 75, 330 and 550 mg/dL.

Table II, below, summarizes the measurement performance results for the initially HUF and subsequently SFF test sensors without compensation and with the HUF compensation system. Table II also summarizes the overall performance results for initially SFF test sensors without compensation and with the initial SFF compensation system for comparison. Table II shows the mean percent bias and thus the percent bias standard deviation determined from both the 648 initially HUF and subsequently SFF test sensors and from the 108 initially SFF test sensors. The percent of the analyses falling within a ±5%, a ±8%, a ±10%, a ±12.5%, and a ±15% percent bias limit in relation to the reference glucose concentration of the blood samples as determined with a YSI reference instrument also are shown.

TABLE II

|  | Mean %-bias | % Bias SD | %-within ±5% | %-within ±8% | %-within ±10% | %-within ±12.5% | %-within ±15% | Analyses |
|---|---|---|---|---|---|---|---|---|
| Initially HUF Comp | 1.88 | 3.46 | 79.0 | 94.8 | 98.6 | 100.0 | 100.0 | 648 |
| Initially SFF Comp | 0.45 | 3.00 | 91.7 | 97.2 | 100.0 | 100.0 | 100.0 | 108 |
| Initially HUF Un-Comp | 0.02 | 24.18 | 16.4 | 26.9 | 34.0 | 40.7 | 40.7 | 648 |
| Initially SFF Un-Comp | −1.76 | 28.63 | 12.0 | 20.4 | 22.2 | 28.7 | 28.7 | 108 |

For approximately 650 or fewer test sensors, use of the HUF compensation system with test sensors that were initially HUF and subsequently SFF placed greater than 95% of the analysis within a ±10% percent bias limit, greater than 90% of the analysis within a ±8% percent bias limit, and greater than 75% of the analysis within a ±5% percent bias limit. This represented a nearly 200% (98.6–34/34*100) improvement at the ±10% percent bias limit and a nearly 400% (79–16.4/16.4*100) improvement at the ±5% percent bias limit in relation to the uncompensated analyses from initial HUF and subsequently SFF test sensors. In fact, similar compensated measurement performance was observed for the initial HUF and subsequently SFF test sensors in relation to initially SFF test sensors.

The use of the HUF compensation system with test sensors that were initially HUF and subsequently SFF also provided a percent bias standard deviation of less than 4 for 650 or fewer analyses performed with 650 or fewer test sensors. This represented a greater than 80% (24.18–3.46/24.18*100) improvement in the percent bias standard deviation in relation to the uncompensated analyses.

These measurement performance results were achieved with a HUF compensation system for whole blood samples having an approximately 20% (volume/volume) to approximately 55% hematocrit content, over a sample temperature range from approximately 15° C. to approximately 35° C., and for glucose concentrations over an approximately 50 mg/dL to 500 mg/dL range. The underfill management system provided these results for test sensors initially HUF and subsequently SFF within 6 seconds or less from the initial fill, within 15 seconds or less from the initial fill, within 30 seconds or less from the initial fill, and within 35 seconds or less from the initial fill. Thus, the HUF compensation system provided a significant improvement in measurement performance to the biosensor system for initially HUF test sensors that were subsequently filled to SFF within approximately 40 seconds.

Figure 10A:
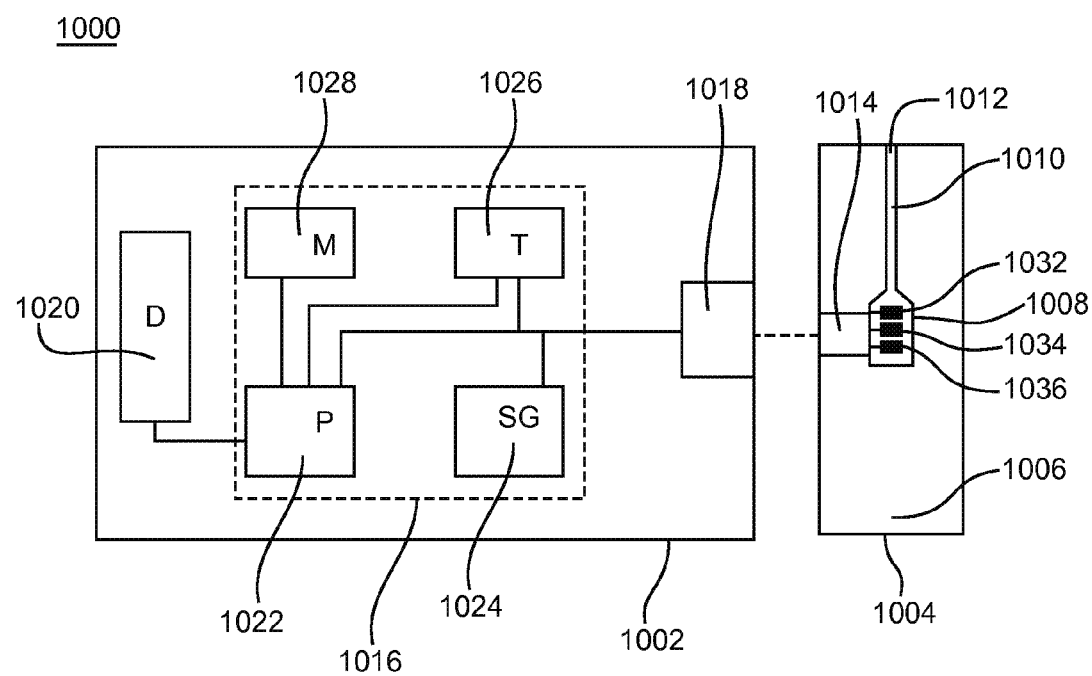
FIG. 10A depicts a schematic representation of a biosensor system with an underfill management system.

FIG. 10A depicts a schematic representation of a biosensor system 1000 with an underfill management system. The biosensor system 1000 determines an analyte concentration in a sample. The biosensor system 1000 may be used to determine one or more analyte concentrations, such as alcohol, glucose, uric acid, lactate, cholesterol, bilirubin, free fatty acids, triglycerides, proteins, ketones, phenylalanine, enzymes, or the like, in a biological fluid, such as whole blood, urine, saliva, or the like. While a particular configuration is shown, system 1000 may have other configurations, including those with additional components.

The underfill management system improves the accuracy and/or precision of the system 1000 in determining the concentration of the analyte in the sample after an initial underfill occurs. The underfill management system includes an underfill recognition system and an underfill compensation system. The underfill recognition system indicates when a sample of the biological fluid has initially SFF or initially underfilled a test sensor reservoir 1008. If the test sensor reservoir 1008 is initially underfilled, the underfill recognition system instructs the system 1000 to request additional sample. The underfill compensation system compensates the analyte concentration for one or more errors in the analysis in response to the initial fill state of the reservoir 1008 as determined by the underfill recognition system.

The biosensor system 1000 includes a measurement device 1002 and a test sensor 1004. The measurement device 1002 may be implemented as a bench-top device, a portable or hand-held device, or the like. A handheld device is a device that may be held in a human hand and is portable. An example of a handheld device is the measurement device of the Ascensia® Elite Blood Glucose Monitoring System, available from Bayer HealthCare, LLC, Elkhart, Ind.

The test sensor 1004 has a base 1006 forming the reservoir 1008 with an opening 1012. An optional channel 1010 may provide fluid communication between the reservoir 1008 and the opening 1012. The reservoir 1008 and channel 1010 may be covered by a lid with a vent (not shown). The reservoir 1008 defines a partially-enclosed volume. The reservoir 1008 may contain a composition that assists in retaining a liquid sample such as water-swellable polymers or porous polymer matrices. Reagents may be deposited in the reservoir 1008 and/or channel 1010. Reagents include one or more enzymes, mediators, binders, and other active or non-reactive species. Test sensor 1004 may have a sample interface 1014 in electrical communication with the partially-enclosed volume of the reservoir 1008. Test sensor 1004 may have other configurations.

In an electrochemical system, the sample interface 1014 has conductors connected to a working electrode 1032 and a counter electrode 1034. The sample interface 1014 also may include conductors connected to one or more additional electrodes 1036 from which secondary output signals may be measured. The electrodes may be substantially in the same plane. The electrodes may be disposed on a surface of the base 1006 that forms the reservoir 1008. The electrodes may extend or project into the volume formed by the reservoir 1008. A dielectric layer may partially cover the conductors and/or the electrodes. A mediator may be disposed on or near the working and counter electrodes. Sample interface 1014 may have other components and configurations.

Measurement device 1002 includes electrical circuitry 1016 connected to a sensor interface 1018 and an optional display 1020. Electrical circuitry 1016 includes a processor 1022 connected to a signal generator 1024, an optional temperature sensor 1026, and a storage medium 1028. Measurement device 1002 may have other components and configurations.

Signal generator 1024 provides electrical excitation signals to the sensor interface 1018 in response to processor 1022. Electrical excitation signals may include the polling and analytic test excitation signals used in the underfill management system. Electrical excitation signals may be transmitted by the sensor interface 1018 to the sample interface 1014. Electrical excitation signals may be a potential or current and may be constant, variable, or a combination thereof, such as when an AC signal is applied with a DC signal offset. Electrical excitation signals may be applied as a single pulse or in multiple pulses, sequences, or cycles. Signal generator 1024 also may record signals received from the sensor interface 1018 as a generator-recorder.

The optional temperature sensor 1026 determines a temperature for use during the analysis of the sample. The temperature of the sample may be directly measured, calculated from the output signal, or presumed to be the same or similar to a measurement of the ambient temperature or the temperature of the measurement device 1002 implementing the biosensor system 1000. The temperature may be measured using a thermister, thermometer, or other temperature sensing device. Other techniques may be used to determine the sample temperature.

Storage medium 1028 may be a magnetic, optical, or semiconductor memory, another processor readable storage device, or the like. Storage medium 1028 may be a fixed memory device or a removable memory device, such as a memory card.

Processor 1022 implements the underfill management system and other data treatment using processor readable software code and data stored in the storage medium 1028. Processor 1022 starts the underfill management system in response to the presence of test sensor 1004 at the sensor interface 1018, the application of a sample to the test sensor 1004, user input, or the like. Processor 1022 directs the signal generator 1024 to provide electrical excitation signals to sensor interface 1018.

Processor 1022 receives and measures output signals from sensor interface 1018. Output signals may be electrical signals, such as current or potential. Output signals include the polling output signals used in the underfill management system. Output signals include the analytic output signal generated in response to the redox reaction of the measurable species in the sample used to determine the analyte concentration of the sample. Processor 1022 may compare the polling output signals to one or more polling thresholds, as previously discussed.

Processor 1022 provides an error signal or other indication of an underfill condition when the sample does not SFF the reservoir 1008 as previously discussed. Processor 1022 may display the error signal on the display 1020 and may store the error signal and related data in the storage medium 1028. Processor 1022 may provide the error signal at any time during or after the analyte analysis. Processor 1022 may provide the error signal when an underfill condition is detected and prompt a user to add more sample to the test sensor 1004. Processor 1022 may stop the analyte analysis when an underfill condition is detected.

The processor 1022 determines underfill compensated analyte concentrations from output signals using a correlation equation as previously discussed. The results of the analyte analysis may be output to the display 1020 and may be stored in the storage medium 1028. The correlation equations between analyte concentrations and output signals and the compensation equations of the underfill compensation system may be represented graphically, mathematically, a combination thereof, or the like. The equations may be represented by a program number (PNA) table, another look-up table, or the like that is stored in the storage medium 1028. Constants and weighing coefficients also may be stored in the storage medium 1028. Instructions regarding implementation of the analyte analysis may be provided by the computer readable software code stored in the storage medium 1028. The code may be object code or any other code describing or controlling the functionality described herein. The data from the analyte analysis may be subjected to one or more data treatments, including the determination of decay rates, K constants, ratios, functions, and the like in the processor 1022.

Sensor interface 1018 has contacts that connect or electrically communicate with the conductors of the sample interface 1014 of the test sensor 1004. Electrically communicate includes through wires, wirelessly, and the like. Sensor interface 1018 transmits the electrical excitation signals from the signal generator 1024 through the contacts to the connectors in the sample interface 1014. Sensor interface 1018 transmits output signals from the sample interface 1014 to the processor 1022 and/or the signal generator 1024.

Display 1020 may be analog or digital. Display 1020 may be a LCD, a LED, an OLED, a vacuum fluorescent, or other display adapted to show a numerical reading. Other displays may be used. The display 1020 electrically communicates with the processor 1022. The display 1020 may be separate from the measurement device 1002, such as when in wireless communication with the processor 1022. Alternatively, the display 1020 may be removed from the measurement device 1002, such as when the measurement device 1002 electrically communicates with a remote computing device, medication dosing pump, and the like.

In use, the biosensor system 1000 activates and performs one or more diagnostic routines or other preparation functions prior to an analysis of a sample. The sample interface 1014 of the test sensor 1004 is in electrical and/or optical communication with the sensor interface 1018 of the measurement device 1002. Electrical communication includes the transfer of input and/or output signals between contacts in the sensor interface 1018 and conductors in the sample interface 1014. The test sensor 1004 receives a sample, preferably the liquid form of a biological fluid. The sample is transferred into the volume formed by the reservoir 1008 by introducing the sample to the opening 1012. The sample flows through the optional channel 1010 into the reservoir 1008, filling the volume while expelling the previously contained air. The liquid sample chemically reacts with the reagents deposited in the channel 1010 and/or the reservoir 1008.

Processor 1022 recognizes when a sample of the biological fluid is present or not present for analysis. Sample interface 1014 provides the sample output signal to the sensor interface 1018. Processor 1022 receives the sample output signal from the sensor interface 1018. Processor 1022 may show the sample output signal on the display 1020 and/or may store the sample output signal in the storage medium 1028. Processor 1022 detects that a sample is present when the sample polling output signal reaches one or more sample thresholds or when electrical conductivity occurs between two or more electrodes. Processor 1022 may detect that a sample is not present when the sample polling output signal does not reach one or more sample thresholds or when electrical conductivity does not occur between two or more electrodes.

Processor 1022 detects when the sample SFF or underfills the reservoir 1008. Sample interface 1014 provides the volume output signal to the sensor interface 1018. Processor 1022 receives the volume output signal from the sensor interface 1018. Processor 1022 may show the volume output signal on the display 1020 and/or may store the volume output signal in the storage medium 1028. Processor 1022 compares the volume output signal with one or more volume thresholds. Processor 1022 recognizes that the sample has SFF the reservoir 1008 when the sequential contact times or volume polling output signal reach one or more volume thresholds. Processor 1022 recognizes that the sample has underfilled the reservoir 1008 when the sequential contact times or volume polling output signal does not reach one or more volume thresholds.

Processor 1022 prompts a user to add additional sample to the test sensor 1004 prior to proceeding with the analysis of the analyte when the processor recognizes that the sample has underfilled the reservoir 1008. Processor 1022 may provide an error signal or other indicator of an underfill condition when the volume output signal indicates the reservoir 1008 is not SFF. The error signal may include a request or symbol requesting additional sample from a user. When a subsequent fill provides more sample to the reservoir 1008 after an underfill, the larger sample volume generates another sample output signal. Processor 1022 determines that additional sample is present when the other sample output signal reaches the same or another sample threshold.

When the processor 1022 recognizes that the reservoir 1008 is SFF, the processor 1022 directs the signal generator 1024 to apply the analytic test excitation signal to the sample. The sample generates one or more output signals in response to the test excitation signal. Processor 1022 measures the output signal generated by the sample from the measured output signal. The processor 1022 determines the analyte concentration of the sample. Depending on the initial and any subsequent fill states determined during underfill recognition by the processor 1022, the processor applies the appropriate underfill compensation. For example, if the underfill recognition system determines initial SFF, initial SFF compensation is applied by the processor 1022. The processor 1022 adjusts the output signals, the correlation between analyte concentrations and output signals, and/or an un-underfill compensated analyte concentration with at least one slope deviation value. The analyte concentration may be determined from the slope-adjusted correlation and the output signal. As described previously, normalization techniques also may be used.

While various embodiments of the invention have been described, it will be apparent to those of ordinary skill in the art that other embodiments and implementations are possible within the scope of the invention.

What is claimed is:

1. A method for determining an analyte concentration in a sample, comprising:
   determining an initial fill state of a test sensor to be an initial underfill state in which an insufficient volume of sample is present;
   signaling for an addition of additional volume of sample to subsequently and substantially full-fill the test sensor with a sufficient volume of sample, the sufficient volume of sample changing the initial underfill state of the test sensor to a subsequent substantially full-fill state;
   applying an analytic test excitation signal to the sufficient volume of sample;
   generating at least one analytic output signal value responsive to the concentration of the analyte in the sufficient volume of sample and the analytic test excitation signal;
   compensating for underfill error in the at least one analytic output signal value in response to the initial underfill state and the subsequent substantially full-fill state of the test sensor, wherein the compensating for the underfill error includes:
      adjusting at least one reference correlation with a compensation system, the compensation system including at least one index function previously determined from an error parameter, wherein the compensation system applies one or more compensation equations in response to the initial underfill state and the subsequent substantially full-fill state of the test sensor; and
      determining an analyte concentration in the sample from the at least one analytic output signal value and the adjusting.

2. The method of claim 1, further comprising detecting sample presence in the test sensor before determining the initial fill state of the test sensor.

3. The method of claim 1, wherein the determining the initial fill state of the test sensor includes:
   applying a polling sequence to the insufficient volume of sample, wherein the polling sequence includes regular and extended polling sequences and the extended polling sequence includes at least one different extended input pulse; or
   sequentially detecting sample filling.

4. The method of claim 3, wherein the extended polling sequence includes two or more different extended input pulses of decreasing amplitude.

5. The method of claim 3, wherein the sequentially detecting includes determining when two different pairs of electrodes of the test sensor are contacted by the insufficient volume of sample.

6. The method claim 3, further comprising selecting the error parameter in response to the polling sequence or the sequentially detecting, wherein the error parameter is a value responsive to a volume threshold.

7. The method of claim 6, wherein the error parameter is a value corresponding to a duration.

8. The method of claim 1, wherein the at least one index function is responsive to a slope deviation between a reference correlation and a hypothetical sample analyte concentration, wherein the hypothetical sample analyte concentration indicates the analyte concentration in the sample without error.

9. The method of claim 1, wherein the compensating the underfill error further includes compensating in response to the initial fill state of the test sensor with a primary function for compensating primary errors in a total error of the subsequent substantially full-fill state, the primary function being different than a primary function otherwise used in compensating errors if the initial fill state was an initial substantially full-fill state, the primary function being a complex index function including at least two terms wherein each term is modified by a weighing coefficient.

10. The method of claim 1, wherein the compensating the underfill error further includes compensating with an initial low volume underfill compensation system including a first residual function for compensating residual errors in a total error, the first residual function being different than a residual function otherwise used if the initial fill state was an initial substantially full-fill state.

11. The method of claim 10, wherein the initial low volume underfill compensation system further includes a primary function for compensating primary errors in a total error of the subsequent substantially full-fill state.

12. The method of claim 1, wherein the compensating the underfill error further includes compensating with an initial high volume underfill compensation equation including a primary function for compensating primary errors in a total error, the primary function being different than a primary function otherwise used if the initial fill state was an initial substantially full-fill state.

13. The method of claim 1, wherein the sufficient volume of sample is whole blood including red blood cells and the analyte is glucose, and greater than 95% of the glucose concentrations determined for 600 or fewer analyses fall within a ±10% percent bias limit.

14. The method of claim 13, wherein the greater than 95% of the glucose concentrations determined for 600 or fewer analyses fall within a ±10% percent bias limit when a test sensor is initially underfilled and subsequently substantial full-filled within 35 seconds or less from the initial fill.

15. The method of claim 1, wherein the sufficient volume of sample is whole blood including red blood cells and the analyte is glucose, and greater than 75% of the glucose concentrations determined for 600 or fewer analyses fall within a ±5% percent bias limit.

16. The method of claim 1, wherein the sufficient volume of sample is whole blood including red blood cells and the analyte is glucose, and the glucose concentrations determined for 600 or fewer analyses provide a percent bias standard deviation of less than 5.

17. A method for determining an analyte concentration in a sample, comprising:
   applying a regular polling sequence and an extended polling sequence to the sample, the extended polling sequence including at least one different extended input pulse;

in response to the applying the regular polling sequence and the extended polling sequence, determining an initial fill state of the test sensor to be an initial underfill state in which an insufficient volume of sample is present;

signaling for an addition of additional volume of sample to subsequently and substantially full-fill the test sensor with a sufficient volume of sample, the sufficient volume of sample changing the initial underfill state of the test sensor to a subsequent substantially full-fill state;

generating at least one analytic output signal responsive to the concentration of the analyte in the sufficient volume of sample;

selecting an error parameter responsive to the at least one different extended input pulse and further responsive to the initial underfill state and the subsequent substantially full-fill state;

determining at least one index function responsive to the error parameter; and determining the analyte concentration in the sufficient volume of sample from the at least one analytic output signal and a slope compensation equation responsive to the at least one index function, wherein the slope compensation equation includes at least one reference correlation and at least one slope deviation.

18. The method of claim 17, wherein the index function is a complex index function including at least two terms wherein each term is modified by a weighing coefficient.

19. The method of claim 17, wherein the error parameter responsive to the at least one different extended input pulse is one of initial binary underfill, initial high volume underfill, or initial low volume underfill.

20. A method for determining an analyte concentration in a sample, comprising:

determining an initial fill state of a test sensor by sequentially detecting sample filling of the test sensor, wherein the sequentially detecting includes determining when two different pairs of electrodes of the test sensor are contacted by the sample, the initial fill state being determined to be an initial underfill state in which an insufficient volume of sample is present;

in response to the insufficient volume of sample, signaling for an addition of additional volume of sample;

in response to the addition of the additional volume of sample, determining a substantially full-fill state of the test sensor by further sequentially detecting sample filling of the test sensor and including determining when the two different pairs of electrodes of the test sensor are contacted by the additional volume of sample;

in response to the determining of the substantially full-fill state of the test sensor, generating at least one analytic output signal responsive to the concentration of the analyte in the sample;

selecting an error parameter responsive to the initial underfill state and the substantially full-fill state when the two different pairs of electrodes of the test sensor are contacted by the sample and the additional volume of sample;

determining at least one index function responsive to the error parameter; and determining the analyte concentration in the sample from the at least one analytic output signal and a slope compensation equation responsive to the at least one index function, wherein the slope compensation equation includes at least one reference correlation and at least one slope deviation.

21. The method of claim 20, wherein the index function is a complex index function including at least two terms wherein each term is modified by a weighing coefficient.

22. The method of claim 20, wherein the error parameter is one of initial binary underfill, initial high volume underfill, or initial low volume underfill.

23. A method for determining an analyte concentration in a sample, comprising:

applying a regular polling sequence and an extended polling sequence to a sample introduced to a test sensor, the extended polling sequence including at least one different extended input pulse;

in response to the applying the regular polling sequence and the extended polling sequence, determining an initial fill state of the test sensor to be an initial underfill state in which an insufficient volume of sample is present;

signaling for an addition of an additional volume of sample to subsequently and substantially full-fill the test sensor with a sufficient volume of sample, the sufficient volume of sample changing the initial underfill state of the test sensor to a subsequent substantially full-fill state;

selecting an error parameter responsive to the at least one different extended input pulse;

determining at least one index function responsive to the error parameter;

applying an analytic test excitation signal to the sufficient volume of sample;

generating at least one analytic output signal value responsive to the concentration of the analyte in the sufficient volume of sample and the analytic test excitation signal;

compensating for underfill error in the at least one analytic output signal value in response to the initial underfill state and the subsequent substantially full-fill state of the test sensor; and determining an analyte concentration in the sample from the at least one output signal value and the compensating, the compensating including determining the analyte concentration in the sample from the at least one analytic output signal and a slope compensation equation responsive to the at least one index function, wherein the slope compensation equation includes at least one reference correlation and at least one slope deviation.

* * * * *